(12) United States Patent
Kraus et al.

(10) Patent No.: US 8,825,149 B2
(45) Date of Patent: Sep. 2, 2014

(54) SYSTEMS AND METHODS FOR MEASURING COMPLEX AUDITORY BRAINSTEM RESPONSE

(75) Inventors: Nina Kraus, Evanston, IL (US); Trent G. Nicol, Kenosha, WI (US); Erika E. Skoe, Chicago, IL (US)

(73) Assignee: Northwestern University, Evanston, IL (US)

( * ) Notice: Subject to any disclaimer, the term of this patent is extended or adjusted under 35 U.S.C. 154(b) by 295 days.

(21) Appl. No.: 13/362,404

(22) Filed: Jan. 31, 2012

(65) Prior Publication Data

US 2012/0197153 A1    Aug. 2, 2012

Related U.S. Application Data

(63) Continuation-in-part of application No. 11/382,805, filed on May 11, 2006, now Pat. No. 8,014,853.

(60) Provisional application No. 61/438,021, filed on Jan. 31, 2011.

(51) Int. Cl.
*A61B 5/0476* (2006.01)

(52) U.S. Cl.
USPC .......................................... 600/545; 600/559

(58) Field of Classification Search
CPC ............. A61B 5/0476; A61B 5/04012; A61B 5/04845; A61B 5/0484; A61B 5/121; A61B 5/126
USPC .......................................... 600/544, 545, 559
See application file for complete search history.

(56) References Cited

U.S. PATENT DOCUMENTS

| | | |
|---|---|---|
| 5,785,653 A | 7/1998 | Kiyuna et al. |
| 8,014,853 B2 | 9/2011 | Kraus et al. |
| 2003/0185408 A1 | 10/2003 | Causevic et al. |
| 2004/0010203 A1 | 1/2004 | Bibian et al. |
| 2004/0243017 A1 | 12/2004 | Causevic |
| 2005/0095564 A1 | 5/2005 | Stuart et al. |
| 2007/0106169 A1 | 5/2007 | Fadem |
| 2011/0313309 A1 | 12/2011 | Nicol et al. |

OTHER PUBLICATIONS

Russo et al. Brainstem responses to speech syllables. Clinical Neurophysiology, 115 (2004), pp. 2021-2030.*
Skoe et al. Auditory Brain Stem Response to Complex sounds: A Tutorial. Ear & Hearing, 2010.*

(Continued)

*Primary Examiner* — Navin Natnithithadha
*Assistant Examiner* — Etsub Berhanu
(74) *Attorney, Agent, or Firm* — Hanley, Flight and Zimmerman, LLC

(57) ABSTRACT

Certain examples provide a method of collecting and analyzing complex auditory brainstem response. The example method includes presenting at least one complex auditory stimulus to a subject and acquiring the subject's complex auditory brainstem response. The example method includes averaging complex auditory brainstem responses from the subject in at least one of a time domain and a frequency domain to form a collected response. The example method includes analyzing the collected response using a signal processor to process the collected response to provide a processed output and to adapt the response for comparison to the at least one complex auditory stimulus. The example method includes performing statistical computations on the processed output to generate visual and data feedback for a user.

19 Claims, 15 Drawing Sheets

(56) References Cited

OTHER PUBLICATIONS

United States Patent and Trademark Office, "Requirement for Restrictions/Election", issued in connection with U.S. Appl. No. 13/218,142, mailed on Mar. 20, 2013, 6 pages.

United States Patent and Trademark Office, "Non-Final Office action", issued in connection with U.S. Appl. No. 13/218,142, mailed on Jul. 8, 2013, 12 pages.

United States Patent and Trademark Office, "Notice of Allowance", issued in connection with U.S. Appl. No. 13/218,142, mailed on Jan. 2, 2014, 18 pages.

Wible et al, "Correlation between brainstem and cortical auditory processes in normal and language-impaired children", Brain (2005), 128, 417-423 (published Jan. 5, 2005).

Galbraith et al, "Brainstem Frequency-Following Responses in Rett Syndrome", Pediatric Neurology. 1996, vol. 15; No. 1, 6 pages.

United States Patent and Trademark Office, "Requirement for Restrictions/Election", issued in connection with U.S. Appl. No. 11/382,805, mailed on Nov. 26, 2008, 11 pages.

United States Patent and Trademark Office, "Non-Final Office action", issued in connection with U.S. Appl. No. 11/382,805, mailed on Jul. 6, 2009, 20 pages.

United States Patent and Trademark Office, "Final Office action", issued in connection with U.S. Appl. No. 11/382,805, mailed on Apr. 28, 2011, 14 pages.

United States Patent and Trademark Office, "Notice of Allowance", issued in connection with U.S. Appl. No. 11/382,805, mailed on Jul. 21, 2011, 15 pages.

Quiroga et al, "Single-trial event-related potentials with wavelet denoising", Clinical Neurophysiology 114 (2003) 376-390.

Wible et al, "Atypical Brainstem Representation of Onset and Formant Structure of Speech Sounds in Children with Language-Based Learning Problems," Biological Psychology, vol. 67, Apr. 2004, pp. 299-317.

Russo et al, "Auditory training improves neural timing in the human brainstem", Behavioural Brain Research (2004), 9 pages.

King et al, "Deficits in Auditory Brainstem Pathway Encoding of Speech Sounds in Children with Learning Problems", Neuroscience Letters, vol. 319, 2002, pp. 111-115.

Bradley et al, "On wavelet analysis of auditory evoked potentials", Clinical Neurophysiology, 115 (2004) 1114-1128.

Dennis L. Molfese, "Predicting Dyslexia at 8 years of age using Neonatal Brain Responses", Brain and language 72, 238-245, (2000).

\* cited by examiner

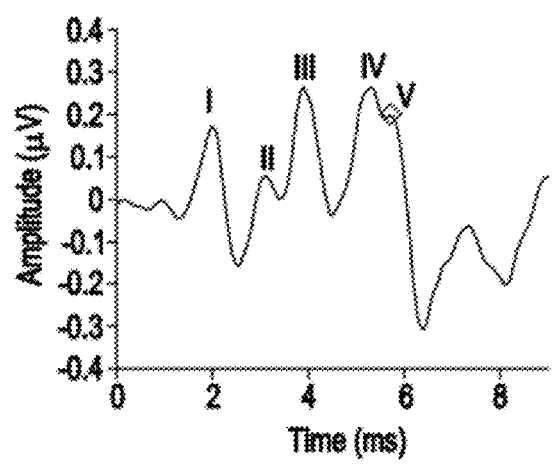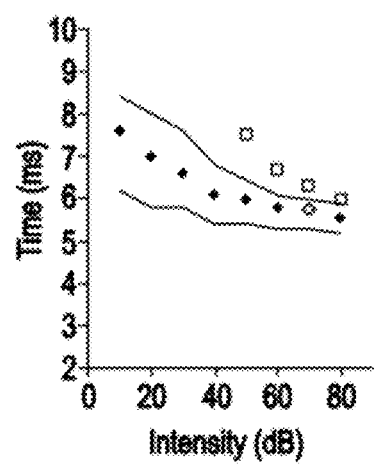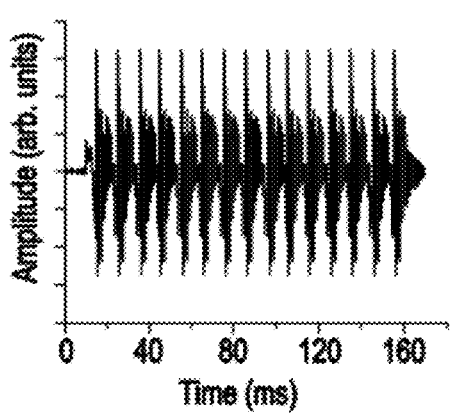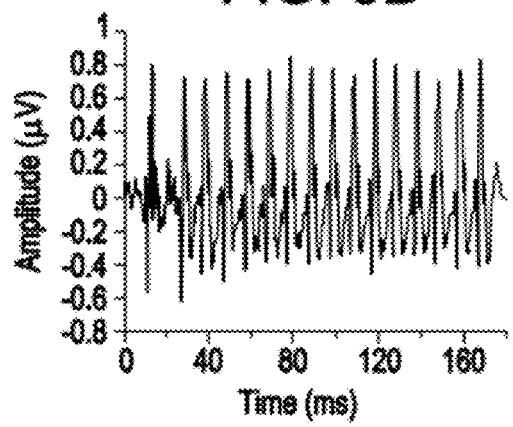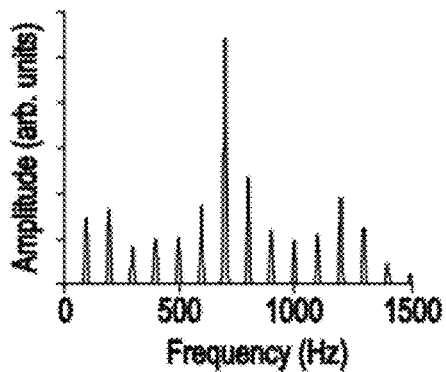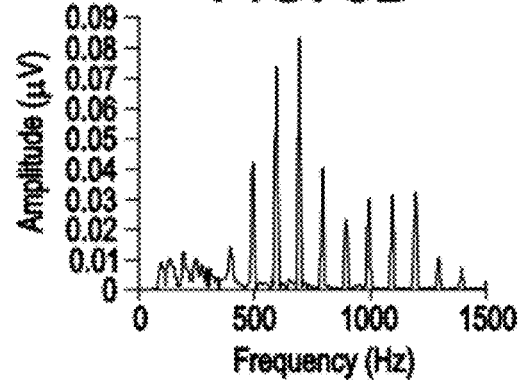

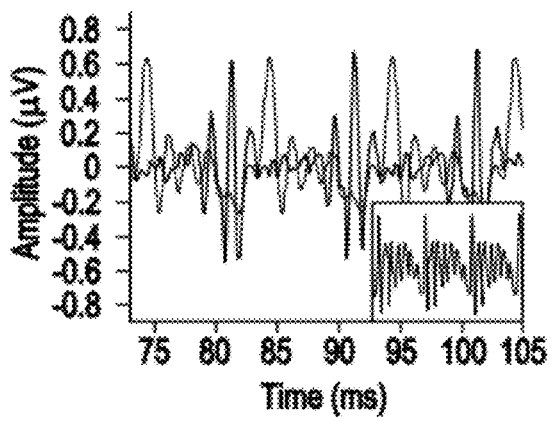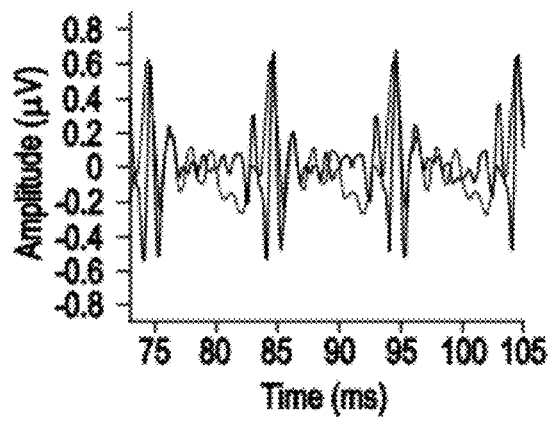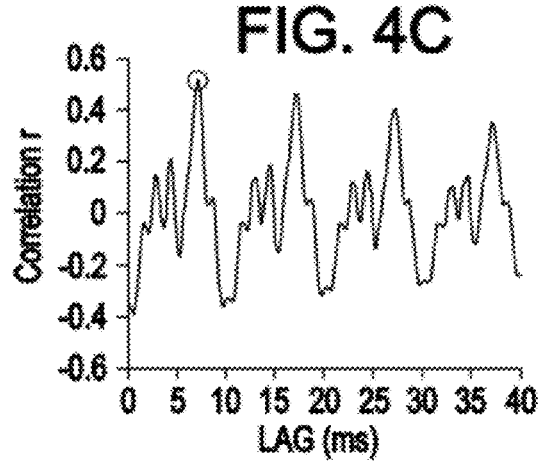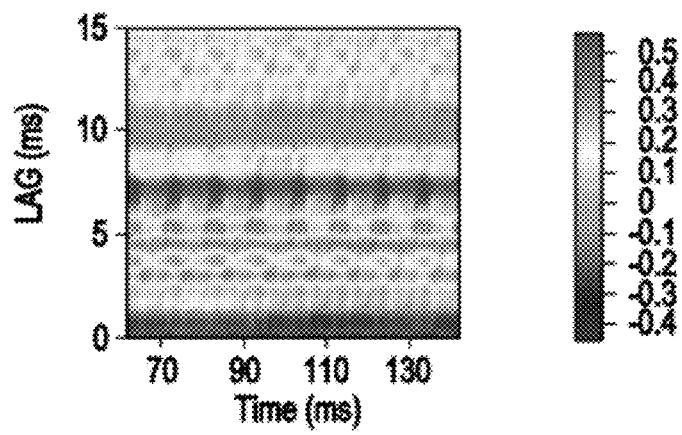

Neural Phase Predictions

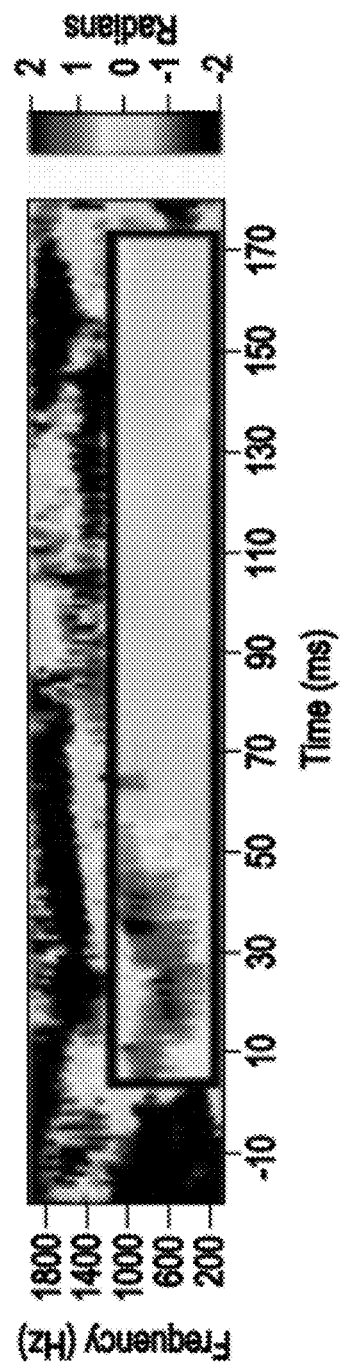

Top: above average ability on HINT
Bottom: below average ability on HINT

SYSTEMS AND METHODS FOR MEASURING COMPLEX AUDITORY BRAINSTEM RESPONSE

CROSS-REFERENCE TO RELATED APPLICATIONS

This patent claims priority to U.S. Provisional Application Ser. No. 61/438,021, entitled "Systems and Methods for Measuring Complex Auditory Brainstem Response," which was filed on Jan. 31, 2011 and is hereby incorporated herein by reference in its entirety, and as a continuation-in-part of U.S. application Ser. No. 11/382,805 (now U.S. Pat. No. 8,014,853), entitled "Neurophysiological Central Auditory Processing Evaluation System and Method," which was filed on May 11, 2006, and is also hereby incorporated herein by reference in its entirety.

STATEMENT REGARDING FEDERALLY SPONSORED RESEARCH OR DEVELOPMENT

This invention was made with government support under Grant No. BCS-0921275 awarded by the National Science Foundation to Northwestern University related to the Impact of Musical Experience on the Nervous System: Development of Sound Transcription, Cognitive Function and Perception; under Grant No. R01-DC010016 awarded by the National Institutes of Health to Northwestern University related to Neural Correlates of Auditory Function and Training in Older Adults; and under NuCAT UL1RR025741, Objective Technology for the Management of Hearing Problems in Older Adults. The government has certain rights in the invention.

FIELD

The presently described technology generally relates to auditory brainstem response. In particular, the presently described technology relates to systems, methods, and apparatus for analyzing complex auditory brainstem response.

BACKGROUND

Recording the brainstem's response to sound can be used to assess integrity of a neural transmission of acoustic stimuli. Transient acoustic events induce a pattern of voltage fluctuations in the brainstem resulting in a waveform that yields information about brainstem nuclei along the ascending central auditory pathway. Accurate stimulus timing in the auditory brainstem is a hallmark of normal perception.

Abnormal perception, understanding and processing of spoken language are fundamental criteria in the diagnosis of many learning disabilities. Currently, central auditory processing disorders are diagnosed through a central auditory processing (CAP) evaluation. Audiologists and speech-language pathologists perform a series of tests, all of which are perceptual and/or audiological in nature (e.g., subjective— not physiological or objective). Auditory brainstem response (ABR) testing provides a physiological indication, but no connection has been established between conventional ABR results and learning disabilities.

Children and adults diagnosed with learning disabilities exhibit highly variable subject profiles. Many factors can contribute to current diagnosis of a learning problem. These include variations in: basic perceptual physiology and higher levels of cognitive function and attention, experientially developed compensatory mechanisms, exposure to previous remedial interventions and differing interpretations of diagnostic categories by clinicians. A consistent and reliable method for diagnosing individuals with learning disabilities has yet to be established.

BRIEF DESCRIPTION OF SEVERAL VIEWS OF THE DRAWINGS

The following detailed description of certain embodiments will be better understood when read in conjunction with the appended drawings. For the purpose of illustrating the invention, certain embodiments are shown in the drawings. It should be understood, however, that the present invention is not limited to the arrangements and instrumentality shown in the attached drawings.

FIGS. 2-6 and 8-14 are representations depicting stimuli and/or evoked brainstem responses.

DETAILED DESCRIPTION OF CERTAIN EXAMPLES

Figure 1:
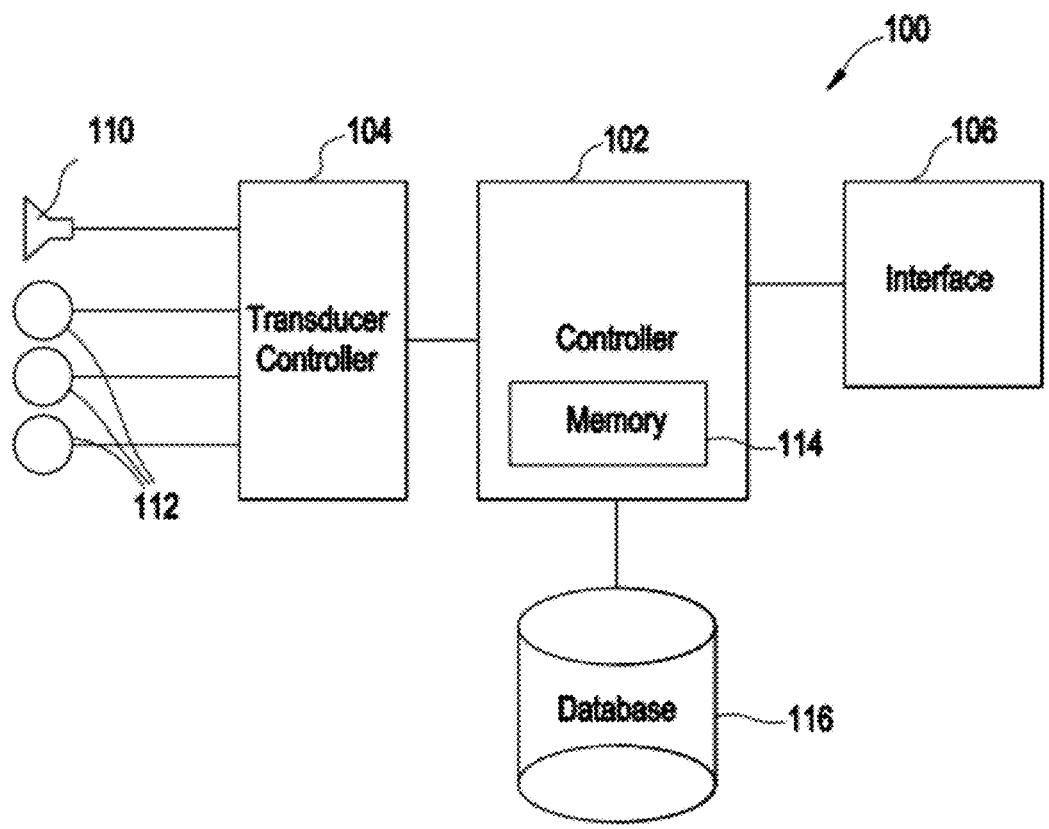
FIG. 1 is a block diagram of a central auditory processing evaluation system.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components can be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in at least one example, at least one of the elements is hereby expressly defined to include a tangible medium such as a memory, DVD, CD, Blu-ray, etc. storing the software and/or firmware.

Certain examples provide a cross-phaseogram, which captures a brain's ability to discriminate between spectrotemporally dynamic speech sounds, such as stop consonants. The cross-phaseogram provides an analysis technique for auditory brainstem responses (ABR) that taps into sub-millisecond temporal precision of the response but does not rely on subjective identification of individual response peaks. Using the cross-phaseogram technique, time-varying frequency differences in speech stimuli manifest as phase differences in ABRs. By applying this automated and objective technique to a large dataset, phase differences are less pronounced in children who perform below average on a standardized test of listening to speech in noise. In certain examples, a cross-phaseogram method can be extended to a wider range of stimuli and populations.

Brief Description

The auditory system is an interactive system, with the auditory brainstem being the hub of this integrated network of ascending and descending projections. Electrical potentials originating in the auditory brainstem can be recorded from the human scalp with electrodes. Traditional auditory brainstem measurements have used stimuli such as clicks and tones. However, research has recently proliferated to include complex sounds such as speech, non-speech vocalization, multi-tone complexes, iterated rippled noise, environmental sounds, musical notes, and melodies, among others.

As described in certain examples, an auditory brainstem response (ABR) to complex sounds (cABR) provides a wealth of information that is unavailable using a click- or tone-evoked ABR. Among the appeals of the cABR are (1) that it reflects incoming auditory signals, resulting in response that maintains a high fidelity to the evoking sound; (2) that responses from auditory brainstem are easily obtainable and interpretable in individuals; and (3) that as part of the interactive auditory system, the brainstem is malleable with experience and training.

To analyze responses to these complex sounds, cABR researchers can utilize a variety of digital signal processing techniques (DSP) beyond those needed for click- and tone-evoked ABRs. In certain examples, a suite of complex stimuli has been developed and a battery of DSP routines that support the collection and analysis of cABRs has been assembled; collectively; this package can be referred to as the "cABR Toolbox". The stimuli in the toolbox include a variety of syllables, such as: a, da, ba, ga, ta, du, mi, spoken with three different Mandarin intonations; notes played by a cello, a tuba and a bassoon; and piano chords. The analysis routines allow for the cABR to be viewed and analyzed in the time and frequency domains in a highly flexible (e.g., user-defined) manner. With this suite of routines, it is, for example, possible to obtain mean amplitude measurements over a user-defined range, to compare the response to the stimulus (via cross-correlation and frequency error measurements), to perform cross-correlation and cross-phase analysis between pairs of responses, and to measure the strength of neural phase locking Because cABRs are rich in temporal and spectral information, the use of multiple measures allows researchers to dissect individual components of the response in terms of how they reflect distinct aspects of processing and to describe the neural encoding of complex sounds in a holistic manner.

In certain examples, systems and methods are adapted to present a short auditory stimulus to a test subject. Commercially available electrophysiological acquisition technology acquires response data from the subject's brainstem response to the stimulus. Evaluation of the response data using various techniques including statistical analysis and comparison to a database of normative results, provides an objective indication of the presence of central auditory processing disorders.

Brainstem timing is exceptionally precise, with deviations on the order of microseconds being clinically relevant. Therefore quantifying the temporal properties of the cABR is central to all auditory brainstem analyses. The timing of brainstem activity has been analyzed traditionally by evaluating the latency of individual response peaks, defined as the time interval between the onset of sound and the elicited peak. Peak identification can present a technical challenge because it is subjective, time consuming, and because it relies on assumptions as to which peaks are relevant for a given stimulus. Moreover, in clinical groups, ABR waveform morphology is often poorly defined. Together, these factors hamper the clinical utility of cABRs, especially when multiple peaks must be identified and/or when responses to multiple complex stimuli are compared.

In light of these factors and the potential clinical applicability of recent findings, a more objective method for extracting temporal information from cABRs can be developed.

An alternative method for describing brainstem timing is to quantify frequency-specific phase information from the cABR. In digital signal processing, phase can be extracted from the output of the discrete Fourier transform, along with the amplitude of each frequency. For an oscillatory signal, phase denotes where the waveform is in its cycle relative to an arbitrary zero (sine or cosine) or relative to a second signal.

Referring to FIG. 1, a system 100 includes a processor or controller 102 coupled to a transducer controller 104, a user interface 106 and a database 108. Coupled to the controller 102 via the transducer controller 104 are an audio transducer 110 and a plurality of electrodes 112. While shown as a single element, transducer controller 104 may be separated into elements 104a and 104b. Element 104a may deliver a stimulus to the audio transducer 110, and element 104b may receive and process brainwave signal information from the plurality of electrodes 112. The transducer controller 104 is any suitable stimulus delivery and data acquisition system, including personal computer-based stimulus delivery and data acquisition systems such as those available from Bio-logic Systems Corporation, Mundelein, Ill. or Compumedics, El Paso, Tex. The audio transducer 110 may be an insert earphone such as the ER-3 insert earphone available from Etymotic Research, Elk Grove, Ill. The electrodes 112 may be Ag—AgCl scalp electrodes, for example, which may be positioned on the test subject from Cz (active) to ipsilateral earlobe (reference) with forehead ground.

The controller 102 may be a personal computer (PC) or other suitable general purpose computing device, or may be a dedicated processor. The controller 102 may include memory 114 within which instructions are retained directing the operation of the controller 102 for carrying out the herein described methods and processes. That is, the controller 102 responsive to a control program retained in the memory 114 operates to generate a test stimulus signal, communicates the test stimulus signal to the transducer controller 104 for generation of an audio stimulus that is presented to the test subject via the audio transducer 110. The controller 102 is further operable to obtain brainstem response data via the electrodes 112 and the transducer controller 104. The brainstem response data may be stored within the memory 114, written to the database 116 and/or presented to a user of the system via the user interface 106. The user interface 106 further permits the user to provide and/or select instructions and/or parameters for the controller 102 for particular test types, testing parameters and/or other data to implement testing.

The database 116, in addition to including a data structure suitable for storage of acquired brainstem response data, may include one or more data structures used to stored data for analysis of the acquired brainstem response data. For example, the database 116 may contain one or more data structures containing normative response data to which the acquired brainstem response data may be compared to provide comparison data. The database 116 may further contain criteria data for evaluating the comparison data for determining the existence in the test subject of a central processing disorder, auditory disability and/or learning disability. The database 116 may still further contain data permitting the recommendation of remedial measures, such as selection of hearing assistive appliances and/or auditory training regimens.

In an example, a test group having a statistically significant membership is used to develop the normative data retained in the database 116. The members of this group are selected based on having no medical or learning difficulties. For example, before acceptance into the test group each member must first meet minimum acceptable criteria on accepted learning and achievement testing as well as on one or more hearing evaluation methodologies, such as, evoked auditory brainstem response tests.

In an example, the testing methodology includes developing a stimulus signal that may be transduced to form an audio stimulus for communication to the test subject. The stimulus signal may include a transient peak element and a sustained element. Such a signal is typical of speech, and for example, the stimulus signal may be a multi-formant synthesized speech sound. In an example, the stimulus signal is a five-formant synthesized /d / having a 40 millisecond (ms) duration.

The audio stimulus may be presented as a single stimulus or as part of a train of stimuli, monaurally or binaurally, with the same or alternating polarities, at constant or varying sound pressure level (SPL), at constant or variable intervals, and in the presence or absence of noise, for example. Criteria for the presentation of the audio stimulus may be dependent on the type of evaluation being performed and the type of disability being screened or identified. The /da/stimulus may be presented in a stimulus train, monaurally, in alternating polarities, at 80 dB SPL to the right ear via an insert earphone, with an inter-stimulus interval of 51 milliseconds (ms), for example. A sound source can also be provided to the non-test ear at less than 40 dB SPL. The stimulus train may include train segments wherein the stimuli within a segment have an inter-segment interval, measured in milliseconds, and the train segments have an inter-train interval, also measured in milliseconds. For example, the 40 ms /d / stimulus may be presented in segments of four stimuli separated by an inter-stimulus interval, e.g., 10 ms, with each segment being separated by an inter-train interval, e.g., 30 ms.

A large number of stimuli may be presented, and corresponding results may be recorded and combined into an average waveform. The above-described data, when gathered from subjectively determined normal test subjects, are indicative of normal auditory brainstem response to a subject stimulus. Thus, these normative data associated with normal response characteristics when stored as part of the database 116 provide a tool for comparison of brainstem response data from a test subject as part of a hearing and/or learning disability or more generally a central processing disorder evaluation system and method.

In operation, the system 100 may be used as a tool for hearing and/or learning disability evaluation. The system 100 may be responsive to a user instruction received via the interface 106 to trigger the controller 102 to initiate a test. The system 100 may be capable of conducting any number of hearing tests, such as, evoked auditory brainstem response (ABR), otoacoustic emission (OAF) and the like in addition to the herein described protocols. Thus, the system 100 may be a robust device for the evaluation and diagnosis of various hearing-related disorders.

An example test may include presentation of an acoustic stimulus (e.g., the /d /stimulus); acquiring brainstem response data from the test subject responsive to the acoustic stimulus; analyzing the brainstem response data to identify response characteristic data; comparing the response characteristic data to a set of normative data to provide comparison data; and determining an existence of a central processing disorder based upon the comparison data.

The control program stored in the memory 114, or otherwise provided to the controller 102, may include at least one data processing routine. The control program may include, for example, three data processing routines. The first routine achieves extraction from the response characteristic data from the brainstem response. That is, the first routine identifies the position of a number of the peaks (e.g., peaks V, A, C and F) in the brainstem response data and records characterizing information regarding the peaks. The characterizing information may include root-mean square (RMS) analysis, Fast Fourier Transform (FFT) analysis, and cross-correlation calculations. The results of these calculations may then be saved to the database 116 to be compared and analyzed in routine two. One example of suitable algorithms for these calculations may be supplied by MATLAB® as produced by The Mathworks, Inc. of Natick, Mass.

The test may optionally include an analysis of subject response in the presence of background noise. The background noise may be in the form of stimuli other than the /d / that may cause an auditory brainstem response. With background noise, the data may be modified to allow more efficient extraction and identification of the peaks. For example, the data may go through a De-Noising Routine. One example of an effective De-Noising Routine may be based on Wavelet Decomposition or any other suitable method such as those described in "De-Noising by Wavelet Transform" by Qian, "On wavelet analysis of auditory evoked potentials" by Bradley et al., or "Single-trial event-related potentials with wavelet de-noising" by Quian Quiroga, et al.

The cABR Toolbox is the first of its kind. While there are a number of systems on the market that can be used to collect evoked potentials (EPs) originating from the brainstem, none have the built-in capacity to record and analyze cABRs in such a sophisticated and streamlined manner.

In the clinical realm, the ABR (to clicks and tone bursts) has been adopted as a valid and reliable means to assess the integrity of the auditory pathway (e.g., measure hearing sensitivity, detect neural pathologies). Currently, while the cABR is increasing in exposure and interest (in both the scientific and general populations), this technology is only being carried out in a few laboratories around the world. A major roadblock to implementing cABRs is that existing commercial technology is not optimized for the collection and analysis of responses to complex sounds. That is, current users of the commercial technology are restricted to performing very basic calculations on the cABR waveform, the kinds of calculations that are applicable for the click- and tone-evoked responses (e.g., latency and amplitude of individual response peaks, simple frequency analyses). Commercial technology can also limit the type of stimulus and the number of stimuli that can be presented. This limit hampers the ability to study how the nervous systems processes complex sounds and soundscapes that are frequency encountered in our daily world.

Certain examples provide reliable systems and methods for recording and analyzing cABRs to a great variety of acoustic stimulation. An example process for the collection, analysis and evaluation of the cABR involves:

(1) Presentation of a complex auditory stimulus (or stimuli) to a subject (either to one ear or both).

(2) Acquisition of a subject's cABR with an EP collection system.

(3) Averaging responses in the time and/or frequency domain.

(4) Submitting the collected response to DSP routines that analyze the response in a variety of manners (latency, amplitude, frequency, and phase) and enable comparisons to the stimulus and to other responses.

(5) Perform statistical computations on the output of (4).

In certain examples, cABR systems and methods can interface with and complement existing commercial evoked-response systems. Complex stimuli at (1) and analysis and statistical techniques at (4) and (5) can be licensed to others for their use. For example, these stimuli and/or processing steps can be integrated with existing third-party hardware and software that accomplishes (2) and (3).

As an objective measurement, the cABR is well-suited for the investigation auditory function in any age-group (neonates to the elderly) and population. In addition to providing valuable insight into auditory processing in the general population, cABRs can be used to study auditory experts (e.g., musicians) and clinical groups (aging, hearing impaired, or dyslexic populations).

Some current and envisioned commercial applications include, for example, using the cABR:

(1) to study the neural basis of reading and hearing in noise;

(2) as a metric of auditory system plasticity across multiple lime courses (e.g., lifelong adaptation arising from language or musical experience; short-term training using in-lab designs or commercial products designed to improve auditory function; on-line modifications to sound processing);

(3) to track systematic neural changes resulting from intervention/remediation;

(4) to investigate audio devices (microphones, amplifiers, speakers, hearing aids, etc.);

(5) to record cABRs in non-standard research environments such as educational and clinical settings; and/or (6) to supplement non-human animal research (e.g., researching the auditory system in genetically-engineered animals, or animals with noise- or lesion-induced hearing losses).

Functionality can be added to currently-available commercial EP systems so that cABR technology might enter the marketplace in a user-friendly format. This would enable cABRs to be adopted by a broader research and clinical community.

In certain examples, hardware and/or software specifications include stimulus presentation, response recording, and response analysis. For example, stimulus presentation includes one or more of the following:

Fast presentation rate (up to 11 per second)
Precise control over time of delivery
Absolute timing accuracy in triggering the recording system
Electrically and magnetically shielded transduction devices such as insert earphones.
Ability to present multiple stimuli in the same sequence along with a way of uniquely coding them for the recording system
Ability to present a simultaneous masker to same ear either in a gated or continuous fashion.

For example, response recording includes one or more of the following:

Differential amplification
Sampling rate at least 10 kHz
Amplitude accuracy of at least 16-bit, with adequate amplification and input range
Filtering bandpass of roughly 70-2000 Hz
Silver-silver-chloride electrodes
Online averaging in time and frequency domains
Online artifact rejection Response processing/analysis may be facilitated in a variety of ways. In certain examples, for all analysis procedures, a user has an option to apply the process to individual trials or to an average of multiple trials.

In a time-amplitude domain, a time-amplitude waveform may be viewed, and timing and amplitude measurements may be obtained for a plurality of peaks and user-defined epochs. These measurements encompass running moving average (RMA), root mean square (RMS), and mean average functions, for example.

In a frequency domain, a waveform is converted to the frequency domain to view and analyze spectrum over a user defined time range. A spectral amplitude may be obtained at a plurality of frequencies and ranges of frequencies. A frequency-domain average may be generated for a group of subjects, for example.

In a time-frequency domain, a waveform is converted to a time-frequency domain to view and analyze spectrogram over a user-defined time range. A frequency contour may be extracted using an autocorrelogram-based process and used to calculate Frequency Tracking measurements (e.g., average deviation between frequency encoding in the response and the stimulus' frequency contour, correlation between stimulus and response contours). An autocorrelogram provides a visual display of the periodicity of sound. Autocorrelation is the cross-correlation of the signal to itself to identify repeated patterns. An autocorrelogram can provide a graphical and numerical autocorrelation function. Frequency tracking measurements may be applied to the fundamental frequency of the stimulus or any of its harmonics. A time-frequency domain average may be generated for a group of subjects, for example.

In a time-lag domain, a waveform is converted to a lag-frequency domain to view and analyze an autocorrelogram over a user-defined time range. A pitch contour may be extracted from the autocorrelogram and use the autocorrelogram to calculate Pitch Tracking measurements (e.g., average deviation in pitch encoding between the stimulus and response contours, correlation between stimulus and response contours). "Pitch Strength" measurements (e.g., an average maximum autocorrelation r-value) may be extracted. A time-lag domain average may be generated for a group of subjects, for example.

In certain examples, cross-correlations may be performed between waveforms (e.g., either over consecutive overlapping time ranges or on a single time range). For example, a stimulus-to-response correlation includes an ability to extract an envelope of a stimulus and perform correlation with the stimulus envelope. A response-to-response correlation may be performed between responses to two different conditions (e.g., response obtain in quiet background versus response obtained in noisy background) or between responses obtained under the same conditions (e.g., inter-trial correlations). Cross-phase analysis may be performed between pairs of responses or between trials. For example, a cross-phaseogram may be generated and analyzed. Waveforms may be exported for processing using third-party software, for example.

Thus, certain examples provide a method of collecting and analyzing complex auditory brainstem response. The example method includes presenting at least one complex auditory stimulus to a subject and acquiring the subject's complex auditory brainstem response. The example method includes averaging complex auditory brainstem responses from the subject in at least one of a time domain and a frequency domain to form a collected response. The example method includes analyzing the collected response using a signal processor to process the collected response to provide a processed output and to adapt the response for comparison to the at least one complex auditory stimulus. The example method includes performing statistical computations on the processed output to generate visual and data feedback for a user.

Certain examples provide a tangible computer readable storage medium including computer program code to be executed by a processor, the computer program code, when executed, to implement a method of collecting and analyzing complex auditory brainstem response. The example method includes presenting at least one complex auditory stimulus to a subject; acquiring the subject's complex auditory brainstem response; averaging complex auditory brainstem responses from the subject in at least one of a time domain and a frequency domain to form a collected response; analyzing the collected response using a signal processor to process the collected response to provide a processed output and to adapt the response for comparison to the at least one complex auditory stimulus; and performing statistical computations on the processed output to generate visual and data feedback for a user.

Certain examples provide a system including a transducer positioned with respect to a subject to provide the complex auditory stimulus to the subject in response to a trigger, the complex auditory stimulus to include a plurality of syllables spoken with different intonations and a plurality of musical notes. The example system includes a plurality of electrodes to detect a complex auditory brainstem response from the subject as a plurality of evoked potentials originating from the brainstem of the subject. The example system includes a processor to provide the complex auditory stimulus and trigger to the transducer and to process the complex auditory brainstem response from the plurality of electrodes. The processor is to process the complex auditory brainstem response over at least one user-defined range to provide time and frequency domain analysis with cross-correlation and cross-phase analysis between a plurality of responses to provide a visualization and output to a user.

Overview

Neural firing recorded from a human scalp with electroencephalogram electrodes can determine whether a sound was heard by that person. Measured electrical impulses originate in the midbrain, a part of the auditory brainstem, and auditory brainstem response (ABR) recording can be used an objective, passive means to determine whether newborn babies can hear.

The detection of a sound by the cochlea of the inner ear initiates a volley of neural firing that progresses from inner ear to midbrain to thalamus to primary sensory cortex and beyond. A normal ABR signal indicates a healthy inner ear because if the cochlea fails to react to the sound, then the neural volley will not take off, the brainstem neurons will not fire, and the electrodes have nothing to pick up.

A click, something like a finger snap, can be used as a stimulus for a probe in ABR hearing assessment. Essentially an impulse with a flat frequency spectrum, the click evokes an ABR with the signature shape shown in FIG. 2A. The timing of specific response peaks is related to hearing sensitivity. In a person with normal hearing, a click presented at a reasonably loud level evokes five clear peaks within about 6 milliseconds of the click's initiation. Identified by Roman numerals I through V, those peaks signal neural firing in sequentially higher-level subcortical structures in the auditory pathway.

For a normal-hearing person, a square-wave click presented to the right ear at an intensity of 70 decibels (dB) reproducibly evokes a response that includes five clinically useful peaks, usually identified by roman numerals. The diamond shown in FIG. 2A identifies peak V, which occurs 5.75 ms after the sound is presented.

In a thorough ABR audiometric evaluation, a clinician presents clicks in a range of intensities first to one ear, then the other. One useful diagnostic is a plot of the time at which peak V arises versus the intensity of the click. FIG. 2B gives simplified plots from a normal-hearing individual and a hearing-impaired one. Peaks that form earlier than V, especially peaks I and III, enable more refined diagnosis. Their presence or absence and the time intervals between peaks I and III, III and V, and I and V help to establish auditory nerve pathology or to distinguish, for example, hearing loss originating in the middle ear from that originating in the inner ear.

The simplified plot here shows the time at which peak V arises, as a function of the intensity of a click presented at time zero. The diamond depicted in FIG. 2B corresponds to that of FIG. 2A. The lines shown in FIG. 2B delimit a time range for normal-hearing individuals. Open squares shown in FIG. 2B illustrate a typical time—intensity relationship for someone with hearing loss. That person, whose hearing threshold is 50 dB, evinced no response below the threshold loudness.

An ABR recording electrode cannot be placed directly in the brain. The best one can do is to attach the electrode to the scalp with conducting paste. The response to a single click is thus swamped by the ongoing electrical activity from all parts of the brain, not to mention artifactual muscle activity and the buzz from nearby electrical appliances. Brainstem response testing, therefore, may employ signal averaging. The peaks shown in FIG. 2A are invariant in that every time a click is detected, the precise voltage pattern of the figure emanates from the brainstem. On the other hand, the larger voltages arising from non-auditory parts of the nervous system, muscle activity, and electrical noise are random. Thus, on averaging over hundreds of clicks, the background noise destructively sums to zero and a response showing the invariant peaks is all that remains. Moreover, because the duration of the recorded brain activity is short—for a click ABR, 10 ms or so—one can rapidly repeat the stimulus.

The clean, interpretable response shown in FIG. 2A is an average over 3000 clicks, for example. With the clicks presented at a rate of 30 per second, the response averaging required less than two minutes. When the presentation rate is further increased or the intensity lowered, peaks I-IV tend to disappear, though peak V and the negative trough following it remain.

A second example ABR stimulus is a short sine-wave tone burst. Whereas clicks serve nicely as an overall probe of hearing, tone bursts provide finer-grained pitch assessment. For example, the sine waves may reveal that low-frequency hearing is normal but high-frequency hearing is abnormal. In certain example, complex ABR (cABR) provides a wealth of information unobtainable from click- or tone-evoked ABR about sound processing in the auditory pathway—including information about experience with language and music. Example reasons for the increasing use of cABR are threefold. First, a reasonably transparent mapping connects the evoking stimulus and the response in cABR. Second, cABR provides information about the efferent auditory system—the downward connections that begin in the cerebral cortex and end in the inner ear. Third, the data can be easily and reliably obtained in individuals.

Stimulus-Response Transparency

As demonstrated in FIG. 2A, the brainstem response to a click does not resemble the square wave that stimulated the response. In the example, the click is nearly instantaneous—e.g., about 0.1 ms long in most ABR systems—but the response evolves over the course of about 7 ms. In contrast, cABRs are elicited by complex stimuli that last several orders of magnitude longer than a click. For most cABR work, stimuli persist for 0.1-0.5 s or so, but some research uses stimuli that continue for several seconds. The response to a periodic stimulus such as a musical note or a speech utterance is essentially the 7-ms-duration response of FIG. 2A repeated over and over again for the duration of the sound. That repetitive neural response to periodic sounds is known as phase locking; phase locking is the property that imparts a striking similarity between stimulus and cABR. For example, taking a cABR and playing the cABR through a loudspeaker, a sound inducing the response can be determined.

FIGS. 3A and 3B illustrate similarity between stimulus and response. Response peaks match up with stimulus peaks, albeit with a short time delay due to neural conduction and synaptic delays between the cochlea and the auditory brainstem. In the sounding of the vowel sound "ah" that generated FIG. 3A, a 10-ms low-amplitude aperiodic transient precedes the high-amplitude periodic vowel. Transients arise from events such as the burst of air as it erupts from between pursed lips in a "p" sound or the striking of a hammer in a piano's soundboard, for example. The left arrow shown in FIG. 3A indicates the initiation of the transient, the right arrow the termination of the vowel sound. Other speech sounds have additional timing cues, such as consonant—vowel transitions, bursts, and other aperiodicities that occur on millisecond or even shorter time scales.

As illustrated in FIG. 3B, corresponding peaks in the cABR are associated with both transient and steady-state auditory phenomena. Different stimuli evoke different cABR transients; which peaks are important depend on the stimulus, the population being studied, and the questions that the researcher is asking, for example. The cABR is dominated by periodic peaks corresponding to the periodic vowel sounding. The response is a mix of low- and high-frequency neural activity reflected, respectively, in the period and shape of the repeated peaks. Also visible in the cABR are peaks, indicated by arrows, that correspond to the vowel's onset and termination.

Other ways of looking at the stimulus and response reveal transparency as well. Any chosen segment of the stimulus and response may be submitted to a Fourier transformation to obtain frequency spectra. For example, to obtain FIGS. 3C and 3D from FIGS. 3A and 3B, the chosen segment of the "ah" stimulus and cABR is the period from 20 to 170 ms. The two frequency spectra are clearly similar, though the auditory structures involved in the response tend to cut off frequencies at the high end of the cABR.

The cABR analysis involves speech, nonspeech vocalizations such as a baby's cry, multitone complexes, music, environmental sounds, and other stimuli. First, studies can employ a variety of digital signal-processing techniques beyond those required for click ABRs. Second, studies can reveal that the brainstem is not just a passive relay station for auditory information. Rather, the brainstem is a hub of ascending (ear to brain) sound processing and descending (brain to ear) modulation of the incoming signal.

Correlation Techniques

In large part, cABR work employs periodic rather than stochastic stimuli. The resulting phase locking lends itself to some familiar digital signal-processing techniques. A simple Fourier transform can reveal information about the spectral energy present in the neural firing. The absolute and relative sizes of the resulting frequency peaks reflect the fidelity with which the sound is being processed. Other methods of processing data yield representations that permit a glimpse of how the spectrum of the response unfolds over time.

Linear correlation techniques result in measures that demonstrate impressive similarity between stimulus and response. One example method of statistically cross-correlating stimulus and response leads to r values that range from $r=1$ for a response that is a copy of the stimulus to $r=0$ for a response with no correspondence to the stimulus.

However, a direct time-domain comparison of stimulus and cABR will not fully expose the similarity of the spectra. First, because the cABR reflects activity in midbrain structures several synapses away from the auditory periphery, high-frequency response tends to be attenuated. Thus, the stimulus should be appropriately filtered if one is to achieve a meaningful correlation with the response. Second, finite neural propagation speed indicates that peaks in the response are delayed in relation to their counterparts in the stimulus. That time lag is evident in FIG. 4A. Shifting the response data by 6.8 ms, as in FIG. 4B, results in a correlation (r value) of nearly 0.6. For example, a lag time that increases or maximizes correlation depends on stimulus, intensity of presentation, and the individual; 6.8 ms is a representative value, for example.

The remaining panels of FIG. 4 give the correlation as a function of time lag, both over the entire period of the recording (FIG. 4C) and for 20-ms segments of the recording (FIG. 4D). Such cross-correlation techniques may likewise be used to compare one response with another. In that manner, a researcher can assess the timing delay introduced in the response by, for example, a faster stimulus presentation rate, a softer intensity of presentation, or background noise.

The fidelity of a complex auditory brainstem response (cABR) to its evoking sound and the similarity of one cABR to another, given similar stimuli, permit correlational analyses. FIG. 4A shows the stimulus (in arbitrary amplitude units) that induced the response in the main plot. Once the stimulus is filtered to approximately match the brainstem's attenuation of high frequencies, the formal similarity between stimulus and response is evident. Nonetheless, the response lags, reflecting neural propagation time. As shown in FIG. 4B, shifting the response earlier in time by 6.8 ms highlights the similarity between filtered stimulus and cABR. A standard statistical analysis yields an r value that describes how well stimulus and response are correlated; for the data plotted here, the correlation is 0.59. The correlogram of FIG. 4C shows the correlation as a function of time lag. The circle indicates the 6.8-ms lag that yields the largest r value. The periodicity in the peaks of the correlation function reflects the periodicity of the stimulus. As depicted in FIG. 4D, to obtain a finer-grained analysis, investigators can determine r values by correlating stimulus and response over short time windows of their choosing. In the correlogram shown in FIG. 4D, the time window is 20 ms long and is centered at the value given by the horizontal coordinate; colors indicate how r values fluctuate over time.

Figure 5A:
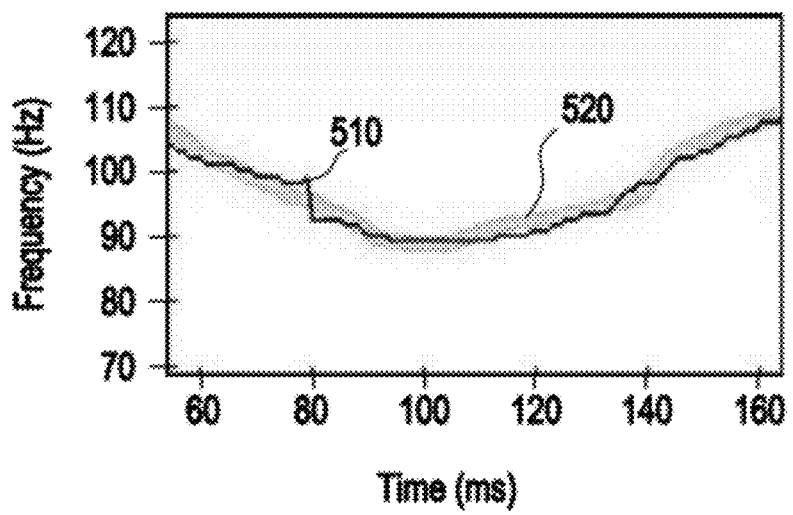

In certain examples, the synthesized syllables that evoked the responses in FIGS. 3 and 4 maintain a steady pitch. That monotone quality is in contrast with normal speech, which commonly includes pitch glides. Some pitch glides are incidental, but some, such as English interrogatives or Mandarin Chinese tones, are mandatory. FIG. 5A illustrates a syllable with a high-low-high pitch contour, not unlike one of the Mandarin tones, and the tracking of the pitch in the brainstem. Short-time Fourier analysis or short-time autocorrelations, such as shown in FIG. 5B, can help expose the neural underpinnings of such pitch tracking.

Figure 5B:
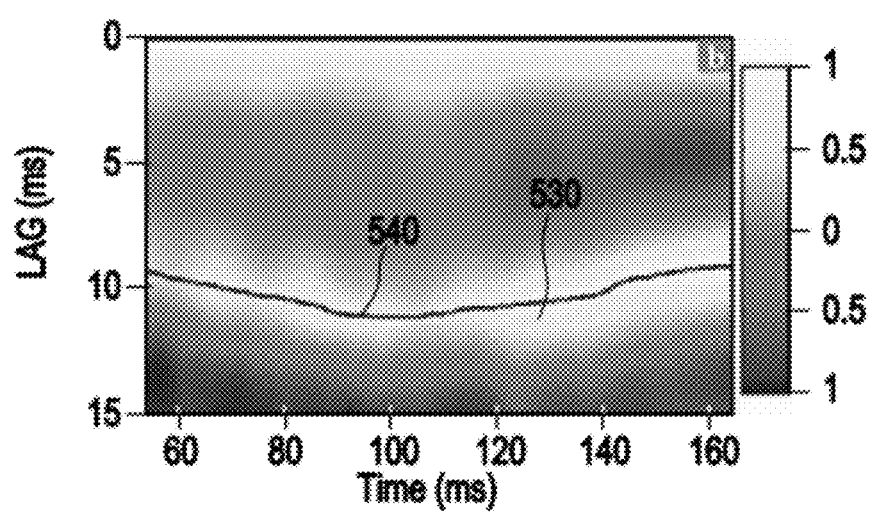

As demonstrated in FIGS. 5A-B, an intonation of a person's voice as he or she asks a question is a common example of a pitch sweep that is linguistically important. Intonation also conveys emotion and a sense of how you mean something. Autocorrelations and other techniques amenable to complex auditory brainstem response (cABR) analysis can track pitch changes in speech. In FIG. 5A, the black curve 510 shows the pitch trajectory (e.g., how the pitch changes over time) of a stimulus similar to a specific tone in Mandarin Chinese. The yellow curve 520 gives the frequency of a cABR as it phase locks to the stimulus's fundamental frequency. The yellow and black curves 510, 520 nearly overlap, which demonstrates the accuracy of the brainstem's pitch tracking In the autocorrelogram of FIG. 5B, colors denote the correlation of the cABR signal and a lagging version of the same signal. The data represent 40-ms windows, with the original signal centered at the value given by the horizontal coordinate. The bright yellow band 530 near the bottom signals the high correlations that occur when the lag nearly matches the fundamental period. The black line 540 corresponds to the stimulus's fundamental period. Autocorrelation techniques can also track overtones of a fundamental (harmonics). The accuracy with which cABR tracks a stimulus's pitch depends on experience and pathologies.

The assessment of timing details in an ABR can be particularly useful in comparative studies that, for example, compare two individuals' cABRs with the same sound or the responses of the same individual with two different sounds. Unfortunately, intricate and complex stimuli often evoke cABRs that do not exhibit the easy-to-identify peaks of an ABR click response. Fortunately, there are techniques that are more sophisticated than visual identification of response peaks. One of those is cross-phase analysis, a technique applicable in particular to cABRs resulting from stop consonants.

As its name suggests, a stop consonant is one formed by a stoppage of air flow through the vocal tract. The interruption is accomplished by, for example, briefly closing the lips for the consonant "b" and by tapping the tongue against the palate for the consonant "d." Despite the obvious mechanical differences in the production of those two sounds, acoustically they are quite similar. With the help of a speech synthesizer, an investigator can strictly control the acoustic dissimilarities between "bah" and "dah," reducing them to subtle differences in overtones caused by the resonance properties of the mouth as speech articulators such as the tongue and lips shift from one consonant to another. A listener would readily distinguish the resulting synthetic syllables as "bah" and "dah," but they actually differ only in their high-frequency content.

Figure 6:
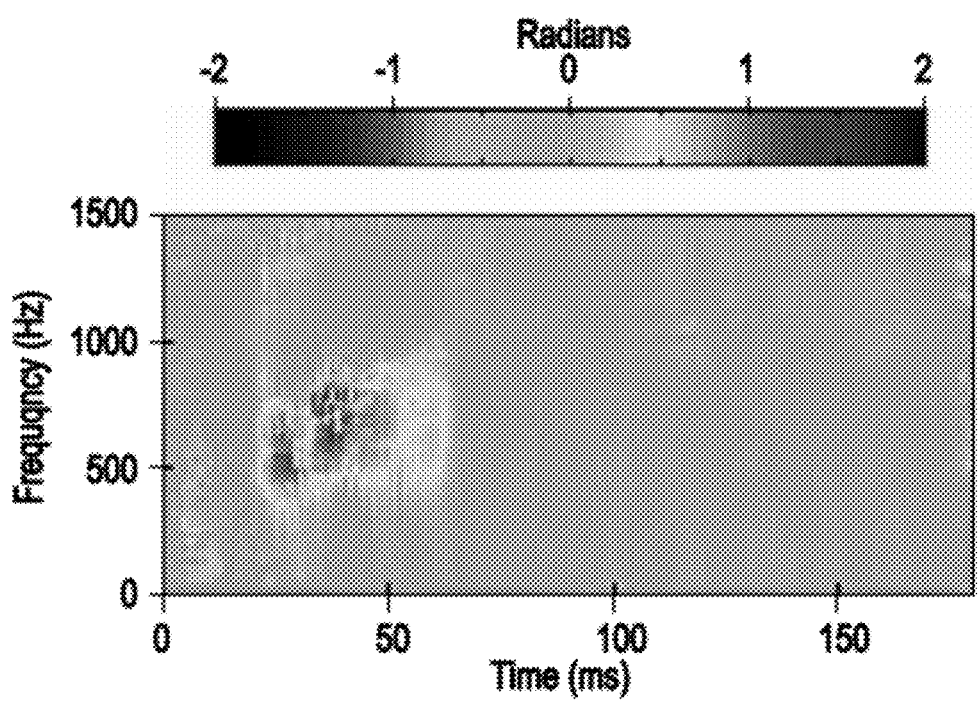

In fact, the frequencies at which the differences occur are greater than the maximum frequency for which the brainstem can achieve phase locking Nonetheless, cABR timing features encode the high-frequency differences. FIG. 6 shows an example of how cABR timing features can encode high-frequency differences. Cross-phase analysis such as that in FIG. 6 uncovers timing differences that are both too subtle and too widespread in frequency to manifest themselves as simple and discrete peak-timing differences. Cross-phase analysis may also be applied to investigate the masking of an auditory signal by background noise.

The sounds "bah" and "dah", for example, are acoustically quite similar, differing only in their high-frequency components. Even though the auditory brainstem cannot phase lock to such high frequencies, its subtly different timing response to the two syllables can be observed, as revealed in the figure. Most of the field is green, corresponding to a common time response. That coherence is to be expected because for most of their duration the two syllables share the acoustically identical vowel "ah." However, the two stimuli are different from 20 to 60 ms; in that portion of the complex auditory brainstem response, warm colors signify that the response to "dah" is slightly earlier than the response to "bah." For any given frequency f, 1 radian corresponds to a timing difference of $1/2\pi f$.

In certain examples, cABR relates to real-life skills such as literacy and the ability to pick out a message in a noisy environment. A cABR reflects life experiences with language and music, for example.

cABR and Experience

Figure 7:
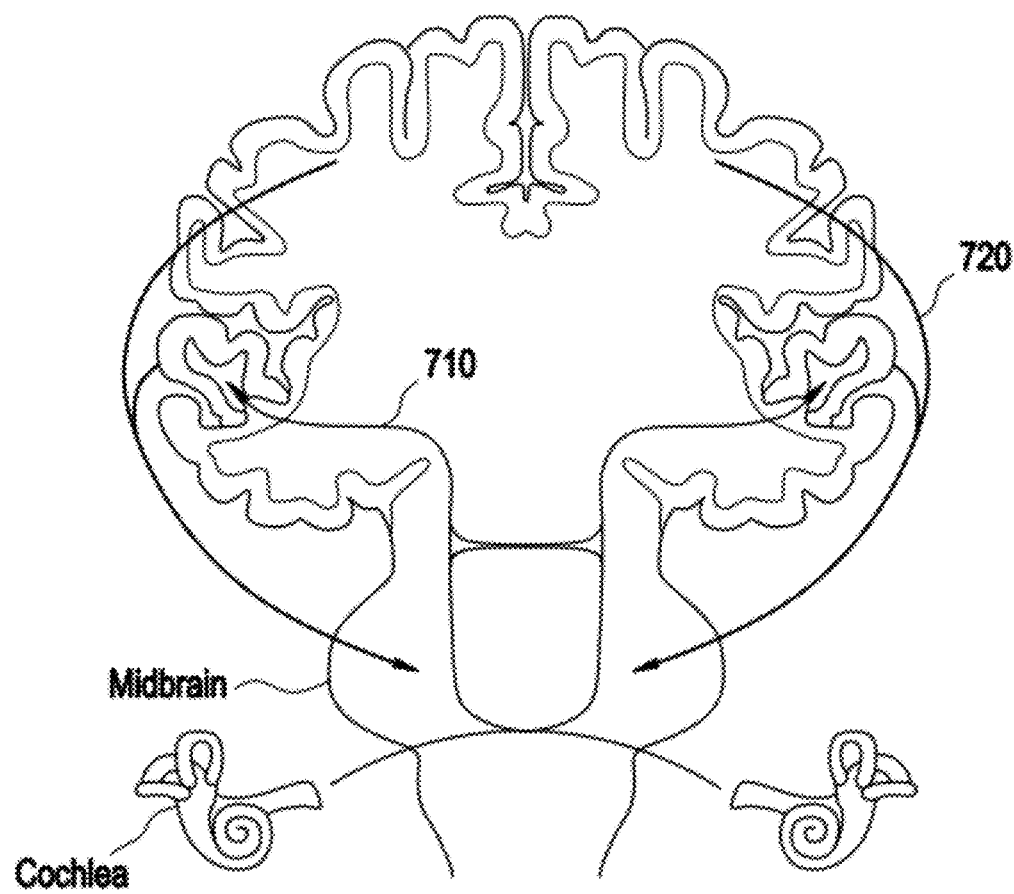
FIG. 7 illustrates a human auditory system including neural routes or pathways that connect the sensory organs and the brain.

The neural routes that connect the sensory organs and the brain run both ways. As FIG. 7 illustrates, an afferent pathway 710 sends information toward the brain, and an efferent pathway 720 sends information toward the sensory organs. Just as the brain "tells" a pianist's fingers how to move, the brain exerts an influence all along the auditory pathway.

As illustrated in the example of FIG. 7, the auditory system is a two-way street. As sound travels along an afferent pathway (thin arrows) 710 from the cochlea to the auditory cortex, the signals are constantly being tuned by "downward" influences (thick arrows) 720. Those influences travel along an efferent network whose paths originate not only in the auditory cortex (darkest shading) but also in non-auditory areas such as the limbic system and cognitive centers of memory and attention. They affect all hubs of auditory processing down to the cochlea, including structures in the auditory midbrain—the primary source of the scalp-recorded complex auditory brainstem response.

Previously, people had assumed that passively evoked ABRs reflected one-way processing—that of the afferent, ear-to-brain path. To a first approximation, that assumption is true for a stimulus such as a click. Because of the signature shape of the click-evoked response and the small amount of variability among individuals, a click ABR is a reliable indicator of hearing sensitivity. A response present and at the right timing indicates normal hearing. A response with delayed timing suggests hearing loss. A lack of response indicates no hearing or perhaps a neuropathological condition.

Afferent processing in the auditory system is only part of the equation. The downward-projecting efferent auditory system also has an effect. Even activity in the hair cells of the cochlea, the peripheral extreme of the chain, is modulated by higher-level processing. A cABR thus represents a snapshot of both afferent and efferent processing; while still a faithful representation of afferent processing, it is modulated by the total of an individual's experience with the evoking sound.

Experience such as language background, is evident in the cABR. A classic example concerns the pitch tracking of Mandarin syllables. In Mandarin, unlike English and other Western languages, the tone of voice helps determine the meaning of a word. Native Mandarin speakers track the pitch changes in Mandarin syllables more accurately than people with no experience with Mandarin or other tonal languages. Experience fine-tunes brainstem structures via an efferent sharpening that originates in the cortex. This idea is in line with the "reverse hierarchy" principle that higher-level cortical structures can sharpen lower-level structures based on a determination of biological relevance. In general, the scientific community is moving away from hierarchical, domain-specific understanding of speech processing toward a picture of an interactive processing system that merges lower and higher structures.

Research has demonstrated that musical experience positively affects broader skills, including those related to motor function, verbal facility, attention, and memory. Musical experience rewires the auditory system, and the cortex influences the brainstem. In certain examples, cABR can be used to examine the effects of musical experience on brainstem processing. For example, highly trained musicians display enhancements in their cABRs, not only to musical sounds but also to speech sounds and non-speech vocalizations.

Thus, there is evidence of basic brain rewiring as a result of music training, which can be used to track music's effect on sensory and cognitive systems. However, only certain sounds induce improved response in experienced listeners, and the enhancements may be evident only in particular features of the cABR—for example, timing but not pitch tracking might be affected.

Example Applications

Features of a cABR can indicate proficiency at real-life skills, including literacy and the ability to listen to speech in a noisy background. To follow running speech, particularly in a noisy environment, the listener needs to organize relevant sounds, such as a companion's voice, into a coherent object or stream while ignoring the rest. That task is accomplished in part with timing and pitch cues. In addition to subjective reporting, various objective tests can assess an individual's ability to comprehend speech in a noisy environment. For example, cABRs can be analyzed with respect to their timing and pitch representation. The quality of those objective representations tracks well with subjective and other objective measures of ability to follow speech amidst noise. The consistency of cABRs with other measures cuts across different ages and even occurs in hearing-impaired individuals.

A correlation can be established between an ability to follow a conversation and brainstem processing. However, literacy, as measured by standardized paper-and-pencil evaluations, also has a relationship with cABR. This relationship is especially striking in children. In particular, response timings are faster and high-frequency components of the response spectrum are stronger, in better readers. In some cases, poor reading may be due to an inadequate efferent sharpening of the lower sensory pathways. The deficiency, discernable in a cABR, prohibits the poor reader from establishing the sound-to-meaning relationships for efficient reading.

As individuals learn to listen better in noise or as they improve their reading skills, their cABRs will reflect those changes. For example, weeks-long training can affect cABR. In some cases, even a single session can lead to measurable change, in accord with the nervous system's sensitivity to patterns in spoken language.

In sum, the auditory brainstem is far from being an inert relay station between cochlea and cerebral cortex. Rather, it incorporates a rich conjunction of ascending and descending neural processes, and cABRs are able to tap into the wealth of information that is found within. Since cABRs reflect not only expertise and experience but also deficiencies in speech perception and reading, clinical applications can both assess auditory function and track the neural changes that accompany exposure or training.

Thus, certain examples provide quantification of influences of neuroeducational outcomes on auditory function. In certain examples, cABR is useful for investigating the auditory effects of such factors as nutrition, exercise, and hormones. As a gauge of biological processes, cABR can assist in the development and fine-tuning of such devices as cochlear implants, hearing aids and other hearing devices, microphones, amplifiers, and speakers. Additionally, application of cABR is not limited to humans; it can provide a probe into auditory physiology in animals. In certain examples, cABR can be leveraged in the lab, in the clinic and in school.

Cross-Phaseogram: Objective Neural Index of Speech Sound Differentiation

Certain examples provide a cross-phaseogram, which captures the brain's ability to discriminate between spectrotemporally dynamic speech sounds, such as stop consonants. The analysis technique for auditory brainstem responses (ABR) taps into the sub-millisecond temporal precision of the response but does not rely on subjective identification of individual response peaks. Using the cross-phaseogram technique, time-varying frequency differences in speech stimuli manifest as phase differences in ABRs. By applying this automated and objective technique to a large dataset, these phase differences are found to be less pronounced in children who perform below average on a standardized test of listening to speech in noise. In certain examples, a phaseogram method can be applied to a wider range of stimuli and populations.

In certain examples, the cross-phaseogram compares the phase of the auditory brainstem response (ABR) evoked to different speech sounds as a function of time and frequency. By being objective and automated and by producing results that are interpretable in individual subjects, these methods are a fundamental advance in both scientific and clinical realms.

Example Stimuli

In certain examples, because the cABR is sensitive to subtle acoustic deviations, synthetic speech can be used to create stimuli that are identical except for the trajectory of the second formant. By isolating the stimulus differences to a single acoustic cue, something that is not possible with natural speech, transmission of this particular stimulus feature by the nervous system can be captured, and this feature is important for differentiating stop consonants.

The syllables [ba], [da], and [ga] can be synthesized using a cascade/parallel formant synthesizer (SENSYN speech synthesizer, Sensimetrics Corp., Cambridge Mass.) to differ only during the first 50 ms, during which each had a unique frequency trajectory for the second formant, for example. In certain examples, the stimuli are otherwise identical in terms of their duration (170 ms), voicing onset (at 5 ms), fundamental frequency (F0), as well as their first (F1) and third-sixth formants (F3-F6). In certain examples, the F0 is constant throughout the syllable (100 Hz) as were F4-F6 (3300, 3750, and 4900 Hz, respectively). During the formant transition region (0-50 ms), F1-F3 changes in frequency as a function of time: F1 rose from 400-720 Hz and F3 fell from 2850 to 2500 Hz. Across the three syllables, F2 begins at a different frequency at time zero but converges at the same frequency at 50 ms (1240 Hz), reflecting a common vowel, for example. In the example, the F2 trajectories are as follows: [ga] 2480-1240 Hz (falling); [da] 1700-1240 Hz (falling); [ba] 900-1240 Hz (rising). A schematic representation of the F2 formant trajectories is found in FIG. 8A. During the steady state region associated with [a], all formants are constant (F1=720 Hz, F2=1240 Hz, F3=2500 Hz, F4=3300 Hz, F5=3750 Hz and F6=4900 Hz) in the example.

Figure 8A:
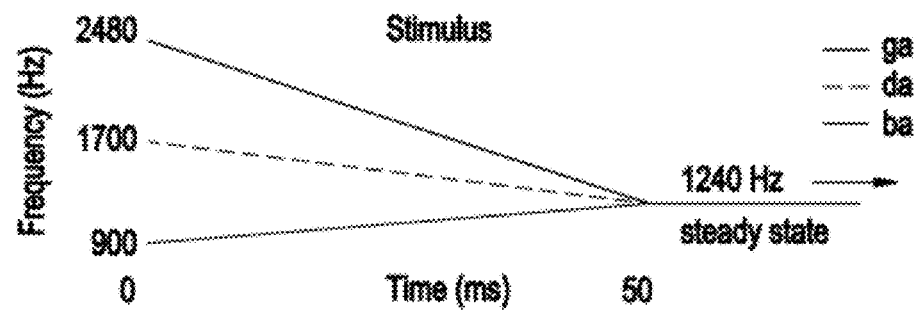
Figure 8B:
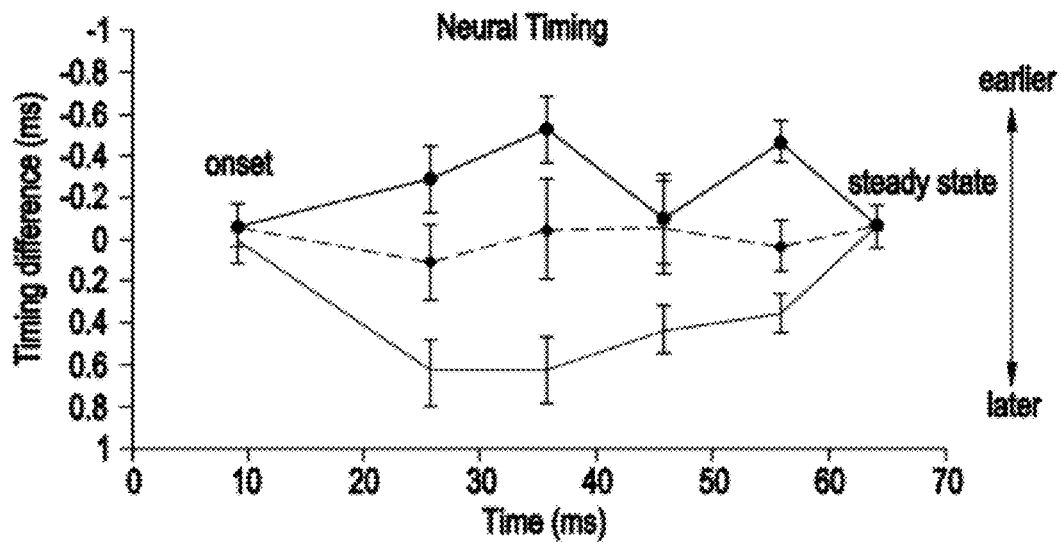
Figure 8C:
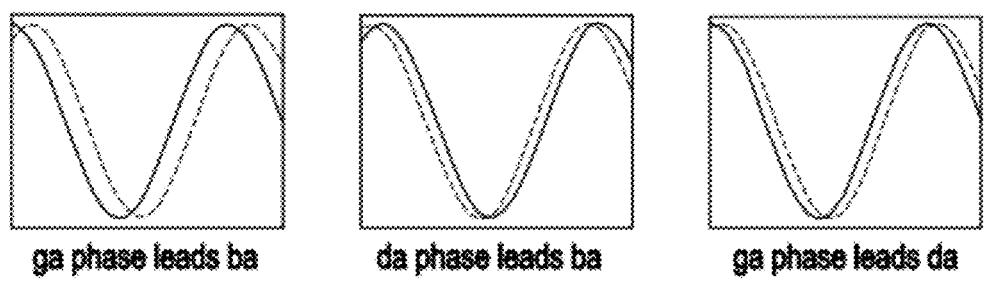

FIGS. 8A-8C depict example methods to compare auditory brainstem responses (ABRs) to different stop consonants syllables (FIGS. 8A-B) and phase shift predictions (FIG. 8C). The frequency differences that differentiate the stop consonants syllables [ga], [da], [ba] (FIG. 8A) are represented in the ABR by timing differences, with [ga] responses occurring first, followed by [da] and then [ba] (FIG. 8B) (e.g., higher frequencies yield earlier peak latencies than lower frequencies). This pattern is most apparent in FIG. 8B at four discrete response peaks between the onset and steady-state components of the response. However, no differences are observed during the onset response (at about 9 ms) and the response to the steady-state portions of the syllables where the stimuli are identical (beginning at 60 ms). As depicted in FIG. 8C, consistent with the pattern observed in the timing of the individual peaks, for a given frequency within the cABR, the [ga] response phase leads both the [da] and [ba] responses. The [da] response phase leads [ba], for example.

Example Electrophysiology and Stimulus Presentation

Auditory brainstem responses can be collected, for example, in Neuroscan Acquire 4.3 (Compumedics, Inc., Charlotte, N.C.) with a vertical montage (active electrode placed at Cz, reference on the earlobe ipsilateral to ear of stimulus presentation, with the ground electrode on the forehead) at a 20 kHz sampling rate. Electrode impedances are kept below five kOhms, for example.

In certain examples, using Stim2 (Compumedics, Inc., Charlotte, N.C.), stimuli are presented to a participant's right ear at 80 dB SPL through an insert earphone (ER-3, Etymotic Research, Inc., Elk Grove Village, Ill.). The stimuli [ga], [da] and [ba] can be presented pseudo-randomly along with five other syllables that had different temporal and/or spectral characteristics. In the example, stimuli are presented using the alternating polarity method in which a stimulus and its inverted counterpart (shifted by 180 degrees) are played in alternating fashion from trial to trial. By averaging responses to the two stimulus polarities, it is possible to reduce or minimize contamination by the cochlear microphonic and stimulus artifact which both invert when the stimulus is inverted. In addition, this adding process emphasizes the envelope-following component of the cABR.

During testing, for example, participants can sit comfortably in a reclining chair in a sound attenuating room and viewed a movie of their choice. The movie sound track, set to <=40 dB SPL, is audible to the left ear. This passive collection technique enables the subject to remain awake yet still during testing and it facilitates robust signal to noise ratios.

Example Data Reduction

In an example, a bandpass filter (70-2000 Hz, 12 dB/oct) is applied to the continuous EEG recording using Neuroscan Edit (Compumedics, Inc.) to isolate activity originating from brainstem nuclei. Averaging can be performed over a 230-ms window to capture neural activity occurring 40-ms before through 190-ms after the onset of the stimulus. In the example, separate sub-averages are created for 3000 artifact-free trials (e.g., trials whose amplitudes fell within a −35 to +35 µV range) of each stimulus polarity; sub-averages are then subsequently added.

Example Cross-Phaseograms

Cross-phaseograms can be generated using, for example MATLAB 7.5.0 (Mathworks, Natick, Mass.) by applying the cross-power spectral density function (e.g., cpsd function in MATLAB) in a running-window fashion (20-ms windows) to each response pair (e.g., [ga] vs.

[ba], [ga] vs. [da], and [da] vs. [ba]). The cpsd function, which is based on Welch's averaged periodogram method, was chosen for its ability to reduce noise from the estimated power spectrum. In an example, 211 windows are compared (per response pair): the first window begins at −40 ms (40 ms before the onset of the stimulus) and the last window begins at 170 ms, with 1 ms separating each successive 20 ms window. Before applying the cpsd function, windows can be baseline corrected to the mean amplitude (e.g., detrend function) and response amplitudes can be ramped on and off using a 20-ms Hanning window (e.g., hann function; 10-ms rise and 10-ms fall). For each of the 211 comparisons in the example, the cpsd function produces an array of numbers, representing an estimated cross-spectral power (e.g., squared magnitude of the discrete Fourier transform) of the two signals as a function of frequency (e.g., 4 Hz resolution). These power estimates are the result of averaging eight modified periodograms that are created by sectioning each window into eight bins (50% overlap per bin). The process of averaging these eight individual periodograms reduces noise in the power estimate by limiting the variance of the power output. To obtain phase estimates for each window, power estimates can be converted to phase angles (e.g., angle function), with jumps greater than $\pi$ (e.g., between successive blocks) being corrected to their $2*\pi$ complement (e.g., unwrap function).

By concatenating the phase output of the 211 bins, a three dimensional representation of phase differences is constructed (e.g., a cross-phaseogram), with the x-axis representing time (reflecting the midpoint of each time window), the y-axis representing frequency, and the third dimension, plotted using a color continuum, reflecting phase differences between the pair of signals being compared. If the two signals do not differ in phase at a particular time-frequency point, this is plotted in green, for example. If signal 1 is further in its phase cycle than signal 2, this is plotted in warm colors, with red indicating a greatest difference, for example. Cool colors indicate the opposite effect of signal 2 being further in its phase cycle than signal 1, for example. In other examples, hashing, shading, and/or other visual distinction can be used to indicate a degree of similarity/difference in phase and/or other characteristic.

In testing, participants can be divided into two groups based on their performance on HINT (Hearing in Noise Test, Bio-logic Systems, a Natus corporation, Mundelein, Ill.), a clinical test that evaluates speech perception in noise, for example. HINT measures the accuracy with which sentences can be correctly repeated as the intensity of the target sentences changes relative to a fixed level of background noise (e.g., speech-shaped noise, 65 dB SPL). The signal-to-noise ratio (SNR) is adjusted adaptively until 50% of the sentences are repeated correctly. The target sentences and noise are presented in free field from a single loudspeaker placed one meter in front of the participant. Target sentences can be constructed to be phonetically balanced, using simple vocabulary and syntactic structure that are appropriate for children at the first grade level, for example. SNRs can be converted to percentiles using age-appropriate norms, for example.

In an example, to compare phase shifts between the two HINT-based groups and across the three stimulus pairings, the cross-phaseogram matrices are split into two time regions (formant transition: 15-60 ms; steady state: 60-170 ms) and three frequency ranges (low: 70-400 Hz, middle: 400-720 Hz, high: 720-1100 Hz) based on the stimulus and recording parameters, as well as the qualitative appearance of the cross-phaseograms (FIG. 9). In the example, each time region is analyzed separately in a 2×3×3 analysis of variance (ANOVA) in SPSS (SPSS Inc., Chicago, Ill.), using 1 between subject factor (Group: TOP vs. BOTTOM HINT performers) and 2 within-subjects factors (RANGE: 70-400 vs. 400-720 vs. 720-1100 Hz, CONTRAST: [ga] vs. [ba], [da] vs. [ba], [ga] vs. [da]), for example. As depicted in FIG. 9, the box demarcates an edge of the noise floor. Phase differences become more erratic above 1100 Hz. Phase differences during pre- and post-stimulus regions are less predictable, due to an absence of responses during these regions, for example.

In certain examples, auditory brainstem responses are recorded to three 170-ms stop consonant speech syllables ([ga], [da], and [ba]) using scalp-electrodes. Responses can be compared by calculating the phase coherence between pairs of responses as function of time and frequency. Cross-phaseograms represent a phase shift between the two signals in a time-frequency plot, with color, for example, signifying the extent of the shift. In certain examples, a response to the stimulus with the higher F2 serves as the first member of the pair ([ga] vs. [ba]; [da] vs. [ba]; [ga] vs. [da]). Consequently, phase shifts have positive values during the formant transition period but are near zero during the steady-state region. Separate analyses can be performed for the response to the formant transition (15-60 ms) and steady-state vowel (60-170 ms) components of the stimulus, for example.

Applying a Cross-Phaseogram Method to an Individual Subject

In certain examples, there are clear cross-response phase differences during formant transition. This is illustrated in FIGS. 10A-C and 11 for an individual subject (e.g., male, age 12) with normal audiometry (e.g., pure tone average of 1.6 dB HL) and language ability. In accordance with the stimulus characteristics, the cross-phaseograms indicate that the response to [ga] phase leads the other responses, with [da] also having phase-lead over [ba]. Cross-response phase differences are minimal during the response to the steady-state vowel portion of the syllables where the stimuli are identical.

Figure 10A:
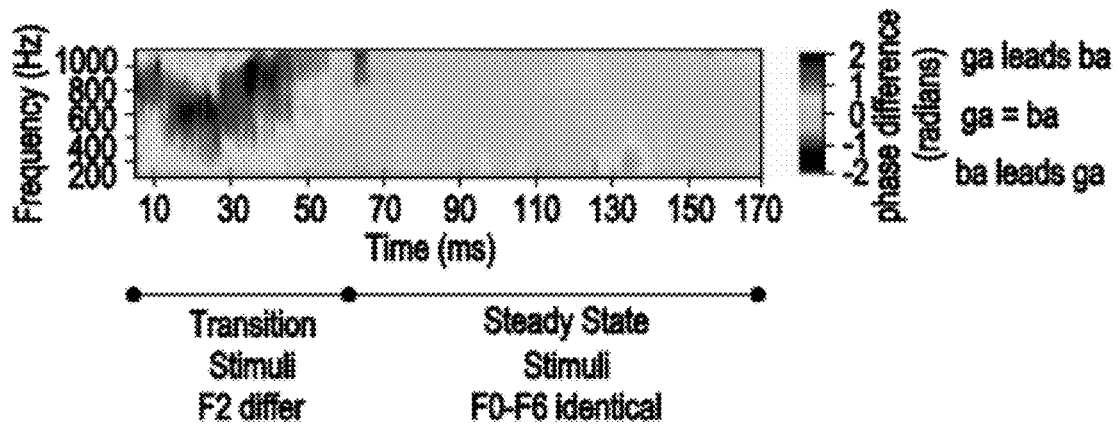
Figure 10B:
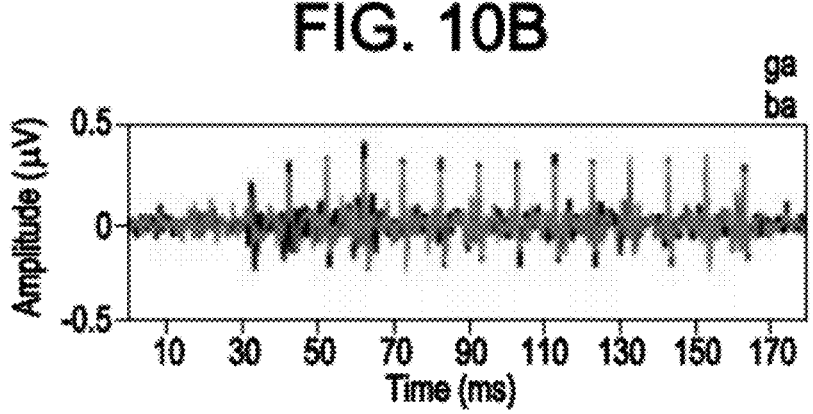
Figure 10C:
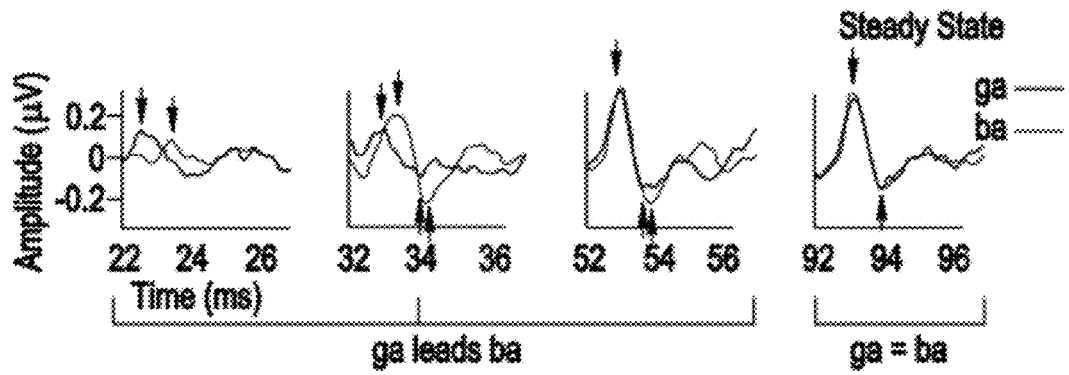

FIGS. 10A-C depict example cross-phaseograms of auditory brainstem responses. A representative subject is plotted to illustrate that individual-subject comparisons are particularly accessible, a feature that makes the cross-phaseogram method clinically useful. This subject (male, age 12) had normal audiometry (pure tone average of 1.6 dB), normal language ability, and he performed at the 87.4th percentile on the Hearing in Noise Test. In FIG. 10A, auditory brainstem responses to the speech sounds [ga] and [ba] are compared using the cross-phaseogram, a method which calculates phase differences between responses as a function frequency and time. In the cross-phaseogram, the time displayed on the x-axis refers to the midpoint of each 20 ms time bin. The y-axis represents frequency and the color axis represents the phase difference (in radians) between the response to [ga] and the response to [ba]. When the responses [ga] and [ba] are in phase, the plot appears green, for example. When the response to [ga] leads in phase relative to [ba], this is represented using yellows, oranges and reds, with dark red indicating the largest differences, for example. However, when the converse is true (e.g., [ba] response leads [ga] response), the plot is represented with shades of blue, with dark blue indicating the greatest phase differences. As can be seen in the plot of FIG. 10A, phase differences between the responses are restricted to the formant transition region (15-60 ms). In the example, the [ga] response phase leads [ba] during this time region. In the response to the steady-state (60 to 170 ms), the responses are almost perfectly in phase.

As shown in FIG. 10B, to enable comparisons between the phase and peak timing measurements, the time domain versions of the response waveforms are plotted (e.g., [ga] in black, [ba] in gray). In the example of FIG. 10C, the responses plotted in the example of FIG. 10B are magnified at four time points (centered at 24, 34, 54, and 94 ms) to illustrate the timing differences between stimuli that are evident during the response to the formant transition region, but not during the response to the steady state portions of the stimuli. Thus, timing differences between responses (FIGS. 10B-C) manifest as continuous phase differences across a range of frequencies (FIG. 10A).

Figure 11:
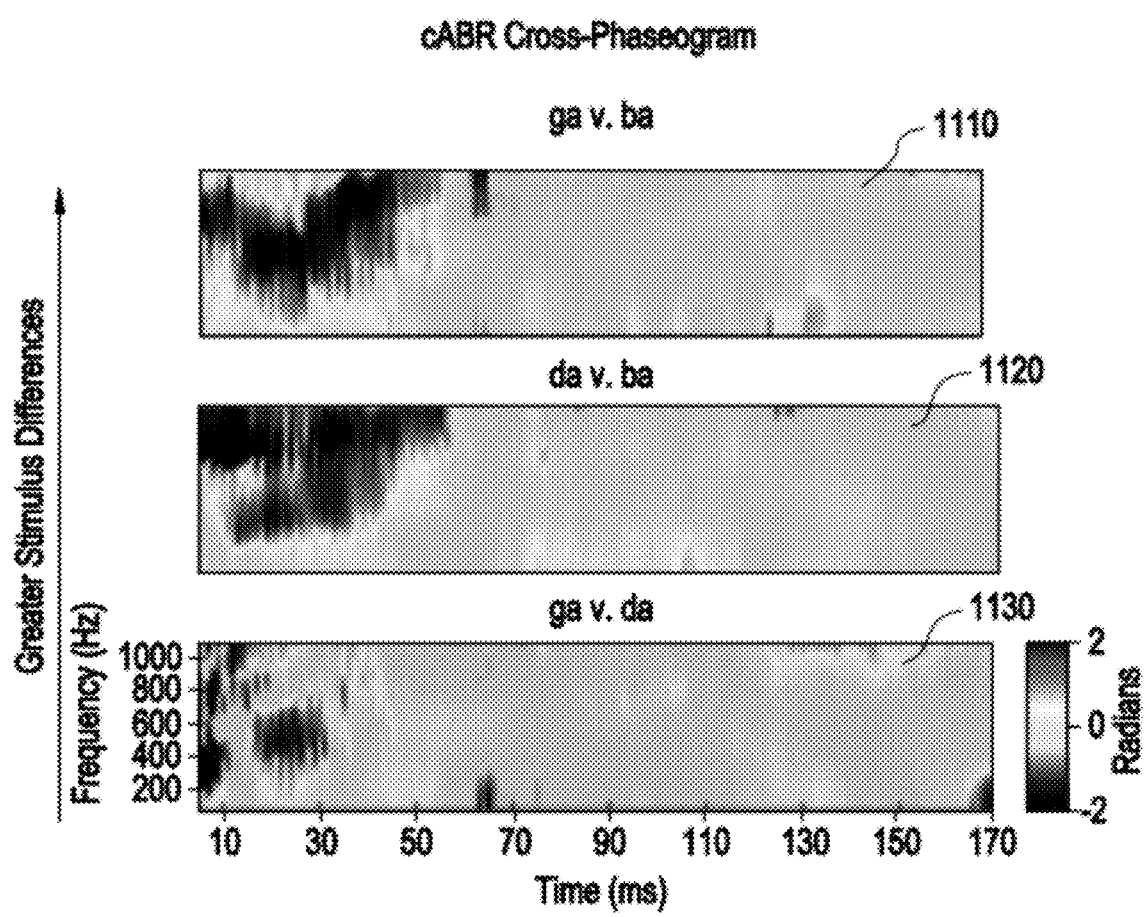

FIG. 11 depicts example response cross-phaseograms for the three stimulus contrasts. For the same representative subject as in FIGS. 10A-C, the top plot 1110 compares the responses to the stimuli which are the most acoustically different ([ga] vs. [ba]) during the formant transition region. In the bottom plot 1130, phase spectra are compared for responses to the stimuli that are most acoustically similar ([ga] vs. [da]). In accordance with these stimulus differences, greater phase differences are observed in the top plot 1110, with more minimal differences evident in the bottom plot 1130. The middle plot 1120 provides a visualization of phase spectra for [da] vs. [ba], for example.

Applying a Cross-Phaseogram Method to a Large Dataset

In certain examples, cross-phaseograms are calculated on a large dataset (e.g., n=90) to evaluate a prediction that cross-response phase shifts are reduced in children (e.g., mean=10.93 years) who perform below average on a clinical test of speech perception in noise (e.g., the Hearing in Noise Test (HINT)). Children performing at or above the 50th percentile on HINT are assigned to the TOP group (e.g., n=40; mean percentile=78.71, s.d.=15.73), and those performing below this threshold are assigned to the BOTTOM group (e.g., n=50; mean percentile 21.15; s.d.=16.52). For formant transition and steady state analyses, within-subjects comparisons are evaluated to validate the results discussed above, and between-subjects comparisons are evaluated to compare the two HINT groups. All phase-shift values are reported in radians.

Figure 12:
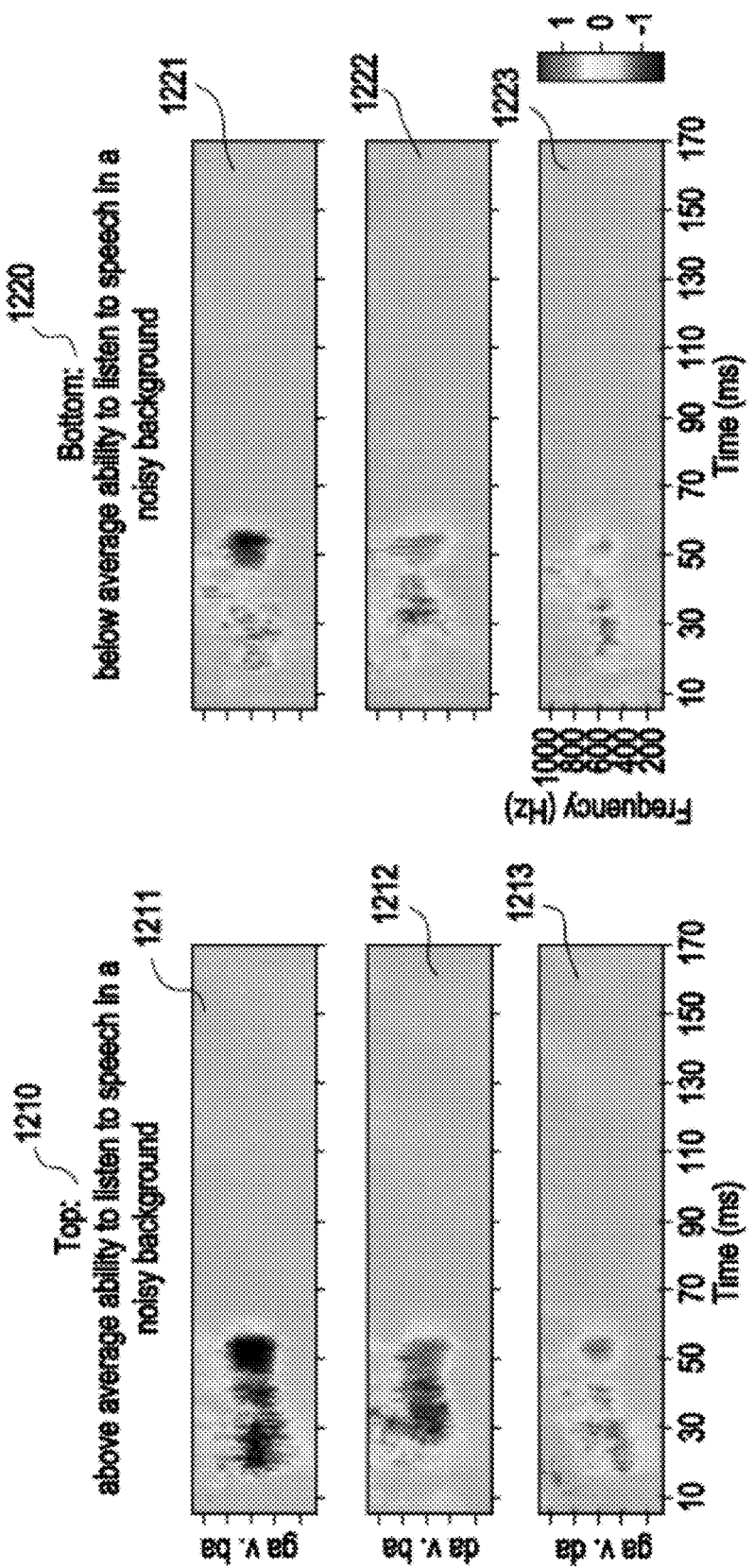

FIG. 12 depicts an example applying the cross-phaseogram method to a large dataset (e.g., n=90). In the example of FIG. 12, children are grouped based on their performance on a standardized test that measures the ability to repeat sentences presented in a background of speech-shaped noise. Across all three stimulus comparisons, cross-response phase differences are more pronounced in the TOP performers (e.g., >50th percentile) 1210 compared to the BOTTOM performers 1220. These plots 1211, 1212, 1213, 1221, 1222, 1223 represent average phaseograms for each group (e.g., an average of 40 and 50 individual phaseograms, respectively). Due to averaging, the phase differences are smaller in these averages compared to the individual subject plotted in FIGS. 10A-C and 11. The color axis has consequently been scaled to visually maximize phase differences. The pattern of effects (e.g., [ga] phase leading [ba], [ga] phase leading [da], and [da] phase leading [ba] during the formant transition region of the responses) is evident for both TOP 1210 and BOTTOM 1220 groups.

Figure 13:
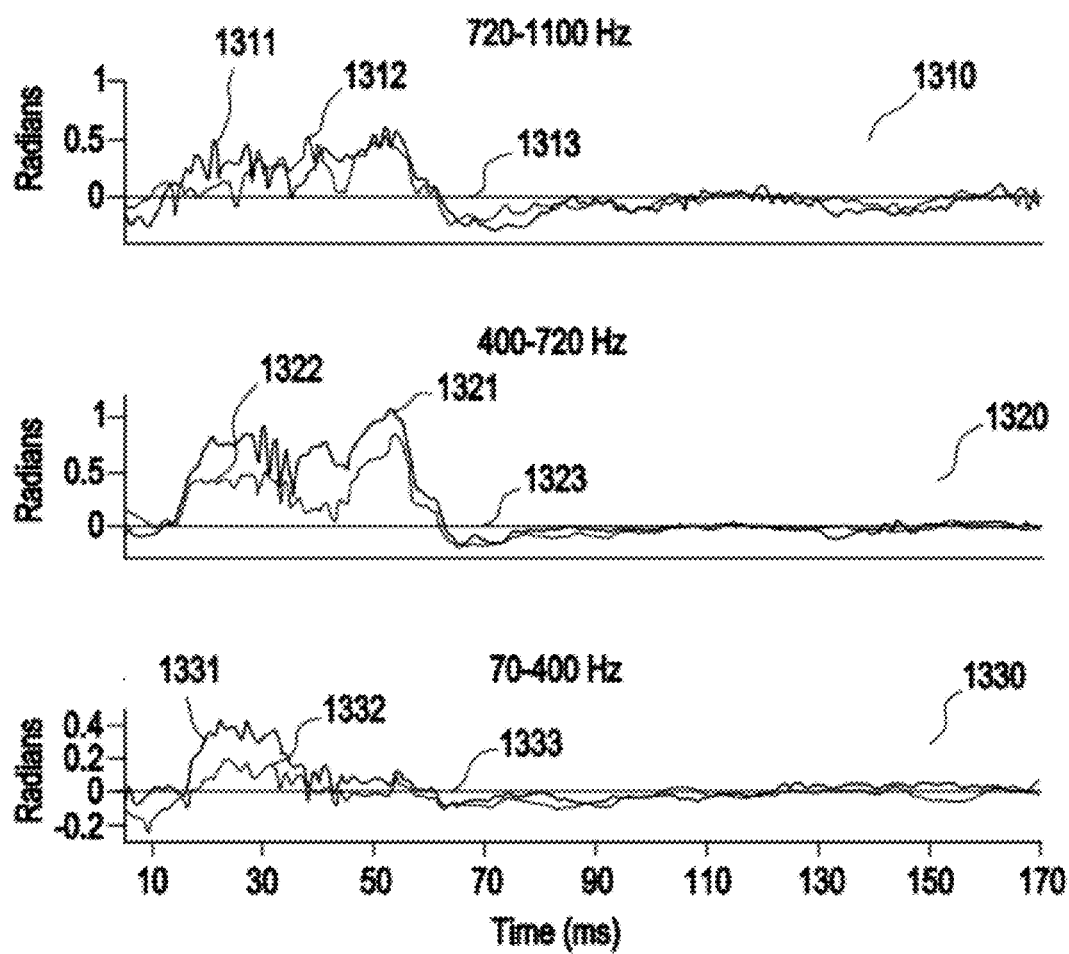

FIG. 13 illustrates deconstructing response cross-phaseograms into frequency bands. Average phase information is extracted over three frequency regions (1310: 70-400 Hz; 1320: 400-720 Hz; and 1330: 720-1100 Hz). In FIG. 13, the comparison between the responses to [ga] and [ba] is plotted for two groups of children, grouped according to their performance on a standardized test of speech perception in noise. Responses for the children performing in the top 50th percentile are plotted in black 1311, 1321, 1331, and the group performing below this cutoff are plotted in red 1312, 1322, 1332. FIG. 13 illustrates greater phase separation among children who perform above average on a speech-in-noise task compared to those performing below average. For each row, the y-axis (radians) is scaled to highlight cross-response phase differences, with zero radians being demarcated by a gray line 1313, 1323, 1333. As would be predicted from FIG. 12, responses to the steady-state portion of the consonant-vowel syllables (e.g., beginning ~60 ms) are characterized by cross-response phase differences that hover near zero radians. During the response to the formant transition region (e.g., 15-60 ms), phase coherence deviates from zero, indicating that the responses differ in phase during this time region. Although the phase differences occur on different scales for each frequency range, within the formant transition region they occur in a consistent direction with the response to the higher frequency stimulus ([ga]) leading the response to the lower frequency stimulus ([ba]) in the pair.

Example Formant Transition—within-Subjects Comparisons

When collapsing across the entire dataset, and all three frequency ranges, unique phase shift signatures can be found for each response pairing (e.g., $F(2,176)=3.875$, $P=0.023$). The extent of the phase shifts is in agreement with the degree of stimulus differences: the greatest phase shifts are found for the [ga]-[ba] pairing (e.g., mean=0.317 radians, s.e.=0.040), and the smallest are found for the [ga]-[da] pairing (e.g., mean=0.208, s.e.=0.028), with the [da]-[ba] pairing falling in the middle (e.g., mean=0.288, s.e.=0.031) (see FIG. 12).

Given the non-uniform nature of the phase differences across the frequency spectrum, average phase-shift values can be calculated for three ranges: 70-400, 400-720 and 720-1100 Hz in the example. A strong main effect of frequency range can be observed (e.g., $F2,176=42.011$, $P<0.0009$), with the middle range having the largest cross-response phase shifts (e.g., mean=1.305, s.e.=0.112), and the lower and higher frequency ranges having smaller, yet non-zero phase shifts (e.g., mean=0.474, s.e.=0.070; mean=0.601, s.e.=0.092, respectively). After correcting for multiple comparisons, the middle range is statistically different from the high and low ranges (e.g., $P<0.0009$, in both cases), whereas the high and low ranges do not differ statistically from each other (see FIGS. 12 and 13). The phase variables in the example follow a normal distribution (e.g., as measured by the Kolmogrov Smirnov test of Normality; $P>0.15$ for all variables).

Example Formant Transition—Between-Subjects Comparisons

In certain examples, children performing above average on the hearing in noise test have more distinct brainstem responses to contrastive speech syllables compared to those performing below average (FIGS. 12 and 13) (e.g., $F(1,88)=6.165$, $P=0.013$; TOP mean=0.328, s.e.=0.035; BOTTOM mean=0.213, s.e.=0.031). The group differences are not driven by one stimulus pairing (e.g., $F(2,176)=1.970$, $P=0.143$). An extent of these differences is also not equivalent across different frequency bands (e.g., $F(2,176)=3.323$, $P=0.038$). When collapsing across stimulus pairings, the groups are most different in the lowest (e.g., $t(88)=3.299$, $P=0.001$; TOP mean=0.7196, s.e.=0.096; BOTTOM mean=0.2772, s.e.=0.092) and mid-frequency bands (e.g., $t(88)=2.480$, $P=0.015$; TOP mean=1.607, s.e.=0.137; BOTTOM mean=1.063, s.e.=0.163), and least different during the highest frequency band (e.g., $t(88)=0.260$, $P=0.796$; TOP mean=0.629, s.e.=0.129; BOTTOM mean=0.581, s.e.=0.130). Taken together, these findings indicate that the stimulus contrasts are more robust over a wider range of frequencies in the TOP group's responses, suggesting that acoustic differences might be represented in a more redundant fashion in the neural responses of children who have better performance on a speech in noise task.

Example Steady-State Region within-Subject Comparisons

In certain examples, while there were no differences between the three frequency ranges ($F(2,176)=2.559$, $P=0.085$) during the response to the steady-state vowel, a main effect of stimulus pairing is found (e.g., $F(2,176)=7.967$, $P<0.0009$). This finding indicates that responses do differ during the steady-state region despite the stimuli being identical. However, because the phase differences during the steady-state region are close to zero, this effect may be the consequence of extremely small variances (e.g., [ga] vs. [ba] mean=−0.055, s.e.=0.009; [da] vs. [ba] mean=−0.014, s.e.=0.009; [ga] vs. [da] mean=−0.021, s.e.=0.007) and the non-normal distribution (e.g., Kolmogrov-Smirnov test of Normality; $P<0.05$ for all variables except the [ga] vs. [da] comparison in the low frequency range). In certain examples, the average cross-response phase shifts are negative, indicating that they occur in the opposite direction from what would be predicted if they represented a "bleed over" from the formant-transition period.

Example Steady-State Region Between-Subject Comparisons

In certain examples, the two HINT groups do not differ during the steady-state region (e.g., $F1,88=0.981$, $P=0.325$; TOP mean=−0.024, s.e.=0.009; BOTTOM mean=−0.036, s.e.=0.008).

Thus, certain examples indicate that the phase of the cABR tracked the linearly ramping frequency trajectory of the stimuli. In comparing response pairs, frequency differences between stimuli manifest as phase-differences, with the higher frequency stimuli producing responses that phase lead responses to the lower frequency stimuli. Moreover, children, who have difficulty hearing in noise, as measured by HINT, tend to have smaller phase shifts between responses than children who perform above average on HINT.

Certain examples describe procedures that permit large-scale analysis of auditory brainstem responses to spectrotemporally complex sounds such as speech. Cross-phaseogram analysis can provide objective methods to access the subcortical basis of speech sound differentiation in normal and clinical populations. Moreover, unlike traditional peak picking methods, the cross-phaseogram is a highly efficient method for assessing timing-related differences between two responses. Using the cross-phaseogram algorithm, time-varying frequency trajectories that distinguish the speech syllables [ba], [da] and [ga] are preserved in the phase of the auditory brainstem response. Furthermore, stimulus contrasts tend to be reduced or minimized in the brainstem responses of children who perform below average on a standardized test of listening to speech in noise but have normal hearing thresholds.

While the measurement of neural phase has long been employed in the field of auditory neuroscience, certain examples provide a technological advance on multiple fronts. Certain examples use a phase-coherence technique to analyze ABRs to spectrotemporally-dynamic acoustic signals. Certain examples provide a method to track how the brainstem represents (or fails to represent) minute changes in stimulus features, including those that are important for distinguishing different speech contrasts. Clinicians and scientists can have access to this information in an objective and automated manner without the need to subjectively identify individual response peaks. In addition to timesavings over manual peak picking methods, use of the cross-phaseogram may also help to streamline data collection time by limiting a number of stimulus presentations to be collected in order to perform reliable temporal analysis on the cABR. Improving the efficiency of the recording and analysis procedures is useful for clinical applications of cABRs.

While the cross-phaseogram method is intended to supplement and not supplant existing analysis techniques, it also offers advantages over other automated techniques. For example, cross-correlation methods (e.g., stimulus-to-response correlation and response-to-response correlation) including running-window versions, offer a more limited view into how nervous system represents different stimulus contrasts. Although they can reveal the extent to which two signals are correlated and the time-shift at which the maximum correlation is achieved, unlike the cross-phaseogram method they do not provide frequency-specific information. Also, because of the non-linear way in which the formant frequencies are captured in the cABR, the stimulus-to-response correlation may, therefore, be a less successful method for tracking how the formant transition manifests in the response. Using the cross-phaseogram method, formant frequencies (e.g., in the range of 900-2480 Hz) that distinguish [ba], [da], and [ga] are "transposed" to lower frequencies in the response, as evidenced by frequency-dependent phase-shifts below 1100 Hz in the three stimulus pairings used in examples above. This provides a unique insight into the non-linear nature of auditory brainstem processing, a finding that may not have been revealed by other methods such as cross correlation.

Certain examples provide a technological and theoretical advance by being the first to link phase-based ABR measurements to the ability to listen to speech in a noisy background. By showing that the cross-phaseogram can be used to investigate the biological underpinning of an everyday listening skill, the cABR has the potential to become a valuable measure of higher-level language processing.

Figure 14:
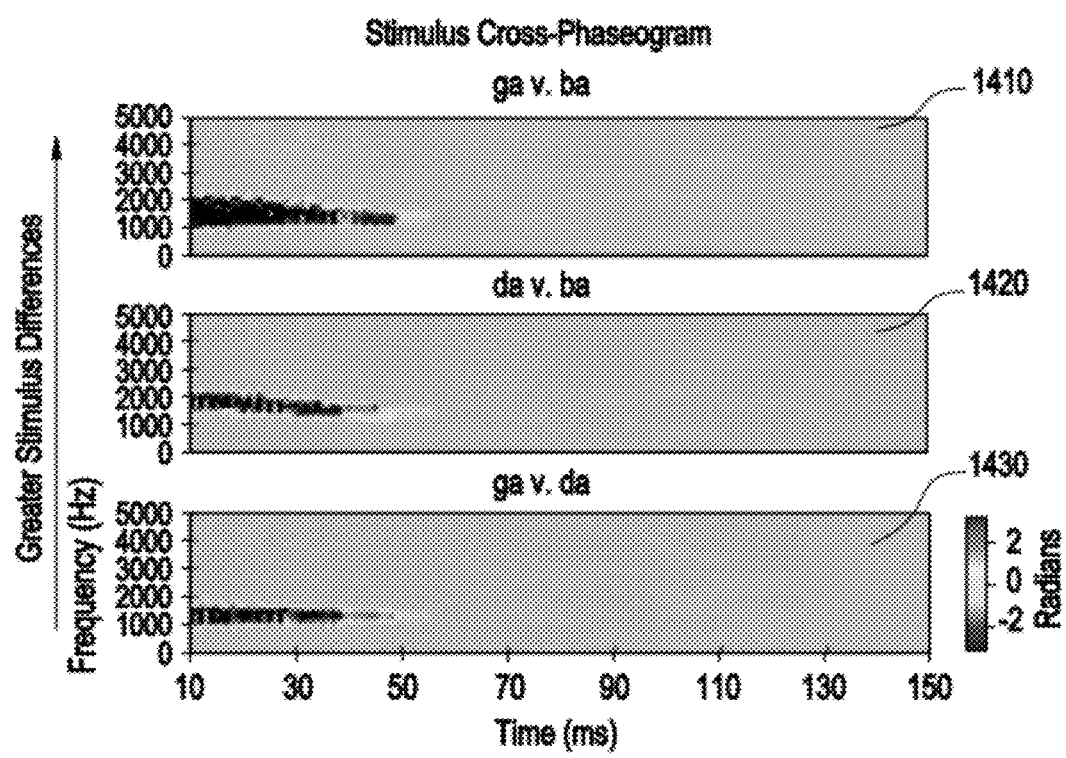

Additionally, as shown in FIG. 14, for example, phase shifts in an auditory brainstem response to different stop consonants likely reflect the differences that exist between stimuli in the amplitude and phase spectra, as well as frequency-dependent neural phase delays resulting from the mechanical properties of the cochlea.

As shown in the example of FIG. 14, cross-phaseograms for [ba], [da], [ga] stimulus waveforms pairings are represented by 1410, 1420 and 1430 in increasing order of stimulus difference from bottom to top. The stimuli differ in the trajectories of the second formant (F2) during the first 50 ms of the response, but are otherwise identical. As can be seen in the stimulus cross-phaseograms 1410, 1420, 1430, phase differences are evident for frequencies between the F2s of the stimulus pairs (frequencies between 900 and 2480 Hz). While temporal information is sufficient for speech recognition in quiet situations, in noisy listening environments, listeners make use of a multitude of other cues, including the amplitude and phase of spectral information. In psychophysical experiments, it has been shown that the phase spectrum conveys many features relating to stop consonant identification, including the structure of the formant transition and the distribution of energy associated with the stop burst. In fact, under certain conditions, the phase spectrum is the only cue needed for identifying stop consonants.

Due to the tonotopic organization of the basilar membrane, traveling waves for high frequency sounds reach their maximum peak of excitation at the base of the cochlea with lower frequencies causing the greatest basilar membrane displacement apically. As such, auditory nerve (AN) fibers innervating the basal end of the cochlea are activated before those at the apex. Consequently, the timing (and accordingly the phase) of the AN response will be different depending on the fiber being stimulated, leading to greater phase delays for fibers with lower characteristic frequencies (CFs). Far field neurophysiological response timing (and consequently phase), in addition to being influenced by the transport time to the characteristic location along the basilar membrane, is impacted by a constellation of peripheral and central factors including: (a) the acoustic delay between the sound source and the oval window; (b) active cochlear filtering; (c) the synaptic delay associated with activating afferent fibers; and (d) the conduction delay between the origin of the neural response and the scalp.

The frequency-dependent timing pattern of single AN nerve fibers is propagated to higher stages of the auditory pathway. As a result, frequency-dependent latency and phase shifts are evident in the scalp-recorded auditory brainstem response (as shown here). This effect has been previously demonstrated for high-frequency tone bursts, amplitude modulated tones and speech syllables. An expansion of the frequency-dependent cochlear delay is also observed for cortical potentials, resulting in greater phase delays than those initially introduced peripherally. However, the extent of this additional delay, which is also seemingly dependent on the spectrotemporal complexity and predictability of the stimulus structure, is highly variable between subjects. Based on work in an animal model, cortical feedback may also modulate human subcortical response timing modulated via the extensive network of corticofugal fibers. Thus, the individual phase-shifts differences reported here may reflect strengthened or weakened reciprocal connections between subcortical and cortical structures that modulate the auditory system's ability to boost stimulus contrasts.

While the factors delineated above account for the existence of phase shifts in the cABR, they do not explain why such phase shifts emerge in the response at frequencies well below those of the second formant (e.g., 900-2480 Hz), the acoustic feature that differentiated the stop consonant syllables. This transposition likely reflects (1) the use of suprathreshold levels, resulting in a spread of excitation across AN nerve fibers of differing CFs and (2) the sensitivity of the auditory system to amplitude modulations (AMs) in the speech signal. As the result of the opening and closing of the vocal cords, the amplitude of the speech formants (spectral maxima arising from the resonance properties of the vocal tract) is modulated at the rate of the fundamental frequency (e.g., 100 Hz) and its harmonics. These amplitude envelope modulations, which are linked to the perception of voice pitch, result from the time-domain interaction of different speech components and they are, as such, not represented in the energy spectrum of the speech signal. However, the amplitude modulation (AM) of the speech signal is relayed by the auditory system through phase locking that is evident in ANs as well as brainstem, thalamic and cortical structures.

In certain examples, using amplitude modulated sinusoids, an elementary model of how brainstem activity represents the interaction of high frequencies (in the range of the F2s used here) and low pitch-related amplitude modulations can be formed. An envelope response can be entrained to the frequency of modulation, but the phase of the response may be dictated by the carrier frequency, for example. For example, response timing was earliest for an 80 Hz modulation frequency when the carrier signal was 6000 Hz, with the timing systematically increasing as the carrier frequency decreased to 3000, 1500 and 750 Hz. Thus, while human brainstem nuclei do not "phase lock," in the traditional sense of the word, to frequencies above ~1500 Hz, brainstem activity conveys the time-varying information carried by high frequency components of the stimuli, such as the differing F2s in the syllables used in this study, through the phase of the envelope response to low frequencies. Certain examples demonstrate this phenomenon for the first time using spectrotemporally complex sounds.

In certain examples, the diminished contrasts between cABR to different speech sounds in some children may reflect reduced neural synchrony and/or diminished sensitivity to amplitude modulations. The diminished cross-response phase contrasts in these children may help to explain why noise imposes a greater effect on them. In addition, stimulus contrasts may be more redundantly represented in the cABRs of children who perform above average on HINT, such that phase-shifts occur across a broader spectrum of frequencies in this group. This redundancy can enable high speech intelligibility for this group of children, especially when the speech signal is masked by noise, for example.

Based on animal models and theories of linguistic-related brainstem plasticity in humans, abnormal auditory brainstem responses to speech may reflect both the malfunction of local processes in the brainstem as well as a maladaptive feedback between subcortical and cortical structures. In this theoretical framework, auditory brainstem activity can influence and be influenced by cortical processes. Consequently, diminished representation of stimulus contrasts in the auditory brainstem could result in poor SIN performance and likewise poor SIN performance could retroactively weaken how stimulus contrasts are coded in the auditory brainstem. However, the currently available cABR collection methods do not permit testing of the separate or combined influences on top-down and bottom-up process on auditory brainstem processing and their relationship to SIN perception.

Thus, certain examples reinforce the proposition that listening in noise depends, in part, on how distinctively the nervous system represents different speech sounds. However, no single factor can explain SIN performance. This is because listening in noise is a highly complex auditory process that depends on the interaction of multiple sensory and cognitive factors. In the case of HINT, a test that requires the listener to repeat back entire sentences, working memory and attention impact performance. In addition, HINT performance may also depend on a child's ability to utilize semantic cues (such as semantic predictability) to overcome the degraded sensory input. Certain examples can help facilitate evaluation of an extent to which phase-based measurements can uniquely predict behavioral measurements of SIN performance and how these relationships might differ across populations.

Examples of cross-phaseogram techniques described above are simply illustrations of how these methods can be used to study auditory processing. Based on these results, cross-phaseograms can be applied to the study of any population or individual demonstrating impaired or exceptional auditory abilities (e.g., the hearing impaired, musicians).

These phase-based methods are appropriate for analyzing subcortical responses to a great variety of other spectrotemporally complex sounds including natural speech, music, and environmental sounds. For example, given that background noise is known to induce delays in the neural response, the cross-phaseogram can complement existing techniques for comparing neural responses to speech in noisy versus quiet listening conditions, which rely heavily on the identification of response peaks. Moreover, because background noise obscures the temporal features of the response, especially the small response peaks that distinguish cABRs to different stop consonants, the cross-phaseogram may provide an avenue for studying the neural correlates of speech sound differentiation in noise. Traditional peak picking methods prohibit or at best hamper this kind of analysis.

Certain examples provide cross-phaseograms as a clinically viable metric in audiological assessment and remediation of noise-induced perceptual difficulties and other language disorders. Cross-phaseogram techniques, which can be used in the evaluation of a large dataset, can also provide the kind of individual-specific information that is essential for such clinical applications but is often inaccessible with other non-invasively employed neural metrics.

Additional Examples for Stimulus Selection and Creation cABRs provide a window into how behaviorally relevant sounds such as speech and music are processed in the brain. Because temporal and spectral characteristics of sounds are preserved in this subcortical response, cABRs can be used to assess specific impairments and enhancements in auditory processing. Notably, subcortical function is neither passive nor hardwired but dynamically interacts with higher-level cognitive processes to refine how sounds are transcribed into neural code. This experience-dependent plasticity, which can occur on a number of time scales (e.g., life-long experience with speech or music, short-term auditory training, online auditory processing), helps shape sensory perception. Thus, by being an objective and non-invasive means for examining cognitive function and experience-dependent processes in sensory activity, cABRs have considerable utility in the study of populations where auditory function is of interest (e.g., auditory experts such as musicians, persons with hearing loss, auditory processing and language disorders).

Stimulus Selection

The following description provides additional example detail regarding stimulus that can be used in cABR collection and evaluation and is provided for purposes of illustration only. Stimulus selection can factor in (1) the population being studied, (2) the specific research questions at hand, (3) electrophysiological properties of the auditory brainstem and (4) the acoustic features that maximize transient and sustained responses.

The syllable /d / is an acoustically complex sound, which begins with a stop burst, characterized by an aharmonic and broadband frication, and is followed by a harmonically rich and spectrally dynamic formant transition. This CV syllable was chosen for a number of reasons. First, /d / is a relatively universal syllable that is included in the phonetic inventories of most European languages. Second, the sound consists of a transient segment followed by a sustained periodic segment. It is, in a sense, much like a click followed by a tone—two acoustic signals whose brainstem response properties have been extensively characterized. Due to these acoustic similarities, the transient onset response to the stop burst is similar to the click-ABR, and the sustained response to the vowel is similar to tone-evoked frequency following response (FFR). Third, stop consonants pose great perceptual challenges to clinical populations such as the hearing- and learning-impaired. Moreover, in noisy backgrounds, because stop-bursts are rapid and low in amplitude compared to vowels, even normal hearing adults and children can find it difficult to discriminate between contrastive stop consonants (e.g., "dare" vs. "bare"). Finally, this syllable elicits clear and replicable auditory brainstem responses.

Transient responses, which are characterized by fast response peaks lasting fractions of milliseconds, are evoked by brief, non-sustained stimulus features such as the onset and offset of sounds. In the case of speech syllables, transient features include the onset of the sound, the onset of vocal chord vibration (i.e., voicing) and the offset of sound. For a simple musical stimulus, such as a bowed note of a violin, transient features include the initial burst of sound created by the bow contacting the string and the offset of sound. The morphology of the cABR onset is dictated by the attack characteristics (e.g., how quickly the sound reaches full volume) of the specific acoustic token. Stimuli with sharper rise times (e.g., abrupt onset/amplitude bursts; clicks) are more broadband (e.g., less frequency specific) and cause broader and more simultaneous activation of the cochlea, which enlists a larger population of neurons to fire synchronously and leads to more robust (e.g., larger and earlier) transient responses. For both speech and music, attack characteristics are important for imparting timbre (sound quality) and they contribute to the identification of specific speech sounds and instruments. Within the classes of speech sounds, obstruent stop consonants (e.g., /d/, /p/, /k/) have, by definition, sharper stimulus onsets than nasals and glides (e.g., /m/ and /y/, respectively) and produce more robust onset responses. Although fricatives and affricates have not been used to elicit cABR (to the best of our knowledge), based on stimulus characteristics we hypothesize the following continuum: earlier and larger onsets for obstruent stops, with affricates (e.g., /t / pronounced "ch"), fricatives (e.g., /z/) and sonorants (a class of sounds comprising nasals, glides and liquids (e.g., /r/ and /l/)) having increasingly smaller and later onsets. Similarly, when choosing a musical stimulus for eliciting cABRs, the specific attack properties of the instrument should be taken into consideration. For example, percussive instruments, like the piano, have fast, steep attacks and bowed string instruments have comparatively smoother attacks. Likewise, the mode of playing an instrument affects the attack (e.g., a plucked string has a shorter rise time than a bowed string). In addition, abrupt changes in the amplitude envelope of the sound also trigger onset-like transient responses. For example, brainstem responses can be recorded to the sound of a baby crying—this particular token included multiple amplitude bursts that produced a series of sharp transient responses.

Sounds containing continuous acoustic features such as sinusoidal tones, harmonically complex vowels, and musical notes elicit sustained brainstem responses reflecting synchronous population-wide neural phaselocking. Using tones (e.g., sinusoids ranging from 250 Hz-2 kHz) each frequency can evoke a unique response, in which the pattern of neural discharge is time-locked to the temporal structure of the eliciting sound. For example, the brainstem response to a 250 Hz tone follows the periodicity of the tone such that response peaks occur at 4 ms intervals (e.g., period=1/frequency; 4 ms=1/250 Hz). For this reason, sustained brainstem responses are often called frequency following responses. Scalp-recorded FFRs can be recorded to frequencies as high as 1.5 kHz, although phaselocking becomes weaker with increasing frequency, reflecting the low-pass nature of brainstem phaselocking. Thus, subcortical phaselocking provides a mechanism for representing low frequencies contributing to pitch and timbre, while a place code likely underlies the neural encoding of frequencies that are too high to elicit an FFR.

To obtain strong sustained responses, the cABR stimulus should have a low pitch with a fundamental frequency (F0) in the range of 80-300 Hz. In speech, the F0 ranges from ~80 Hz for a deep male voice to ~400 Hz for a child. While speech can contain spectral information up to 10 kHz, the spectral information necessary for distinguishing different consonants and vowels is largely below 3000 Hz. When selecting a speech-phoneme for cABR recording, keep in mind that some speech formants, including the second formant of many vowels, are above the range of brainstem phaselocking and may not be observable in the response. A wide range of frequencies is also encountered in music. For example, the lowest note on a standard 88-key piano occurs at 32.70 Hz and the highest at 4186 Hz. Because the F0s of instruments are generally higher than speech, they often fall outside the limits of strong brainstem phaselocking. Therefore, it may be necessary to use an instrument within this cABR target range, such as the trombone.

Real-life sounds, unlike sine waves, have non-stable F0s and harmonics, and complex harmonic structures. For time-varying stimuli, such as diphthongs, consonant-vowel formant trajectories, musical glissandos, and tone language pitch contours, cABRs follow even small changes in frequency with inter-peak intervals systematically increasing or decreasing with changing frequency. For harmonically complex sounds, phaselocking is observed to the frequencies physically present in the stimulus, as well as the frequencies introduced via nonlinear processes within the auditory pathway. Examples include phaselocking to the amplitude envelope and distortion products.

During speech production, sound is produced when air leaving the lungs causes the vocal chords to vibrate. For speech, the F0 is determined by the rate of this vibration. Because the vocal chords close more slowly than they open, the sound that is produced is not a sinusoid. It is instead a complex waveform, resembling a triangle or saw-tooth wave, containing harmonic energy at integer multiples of the F0. This harmonically rich sound is then filtered (e.g., shaped) by the speech articulators (e.g., teeth, tongue, lips, etc.) to form different speech sounds. Different articulator configurations change the resonance properties of the vocal tract causing certain harmonics to be amplified and others to be attenuated. Formants, which correspond to peaks in the spectrum, arise from this filtering. Each speech sound can be uniquely identified by its characteristic formant pattern, with the first two or three formants being sufficient for identifying most speech sounds. The cABR, which synchronizes to the F0 and harmonics of the speech waveform, contains greater energy for harmonics coinciding with formants because there is more energy in the signal at these frequencies. In other words, brainstem nuclei perform a type of "formant capture", whereby harmonics adjacent to the formant regions are emphasized. Also, note that in the speech spectrum, that the F0 has less energy than the speech-formants (e.g., in FIG. 3C, compare an amplitude of F0 at 100 Hz to F1 at 700 Hz). However, because the opening and closing of the vocal folds produces a signal that is naturally amplitude-modulated, F0 and other modulating frequencies are introduced into the neural system during nonlinear cochlear processing.

In contrast to speech, which is dominated by fast spectrotemporal transitions, music has more sustained temporal and spectral elements, slower transitions, and finer frequency spacing. In music, the mechanism of F0 generation depends on the instrument. For example, the reed is the source of F0 vibration for the oboe and clarinet, whereas the string is the source for the violin and guitar. In the same way that speech sounds are characterized by unique formant configurations, instruments also have characteristic harmonic structures that impart timbre. Specifically, the timbre of a musical sound is determined by the rise time of the attack, the spectral flux (e.g., change in harmonics over time) and the spectral centroid (e.g., the distribution of the harmonics). The clarinet, for example, has a lower harmonic structure dominated by odd harmonics (the even harmonics have been attenuated). The flute, saxophone, trombone and tuba, which are all characterized by strong odd and even harmonics, can be differentiated by the distribution of the harmonics (e.g., the energy of the tuba is concentrated in the lower harmonics).

The harmonic structure of musical sounds is partially preserved in the response. Generally speaking, FFRs are more robust when there is less spectral flux (i.e., brass and woodwind families. The timbre of a musical instrument also depends on how quickly the sound decays (e.g., a piano has both a fast onset and quick decay while an electric piano has a slower onset and decay). For the purposes of eliciting an FFR, sounds with longer decays elicit responses that are more sustained.

Within the speech-ABR literature, the length of vowel stimuli has varied between 60 ms to 2 seconds and for CVs from 40 to 500 ms. In experiments using musical stimuli, the duration has ranged from 170 ms for a 2-note musical interval to 1.1 seconds for a five-note musical melody.

Because of the sheer number of stimulus presentations to obtain a robust response, there is an obvious tradeoff between stimulus duration and length of the recording session. For example, to record 6000 trials to a synthesized 40 ms /d / takes approximately 9 minutes, assuming an interstimulus interval (ISI) of 50 ms. Yet natural sounds generally occur on the order of seconds and not fractions of seconds, which necessarily requires much longer recording sessions. A factor limiting the stimulus duration is the feasibility of having a subject remain still for a long time. Thus, stimulus duration may be restricted in order to present the desired number of stimuli in a reasonable amount of time. For speech syllables, one tactic is to record ABRs to a stimulus containing the consonant and consonant-vowel transition (CV) without a steady-state vowel. Because each consonant-vowel pair has a unique formant transition, the steady-state vowel can be removed with little impact on the percept. In fact, musical timbre and vowel identity can be accurately determined from 1-4 cycles of the F0 but pitch identification requires at least four cycles. Stimulus duration greatly affects pitch because lower frequencies have longer periods than higher frequencies (e.g., a 20 ms stimulus can have no meaningful frequency representation under 50 Hz).

Stimulus Creation

With modern computers, recording natural sounds is relatively simple. The process requires a sound-attenuated chamber, a microphone, a high resolution sound card and software for recording (e.g., Adobe Audition, Adobe Systems, Inc., San Jose, Calif.). To help ensure that a viable token can be extracted, multiple recordings, and when possible, multiple speakers/instruments should be used. Both natural and synthetic sounds should be created with a high digitization rate (e.g., >20 kHz). However, because some stimulus presentation systems require a specific sample rate, the recordings may need to be resampled. Likewise, when comparing the stimulus and the response via cross-correlation the two signals must have the same sampling rate. For these reasons, it is best to sample at a high rate so that upsampling is not necessary.

Although natural speech and music tokens are ideal in the sense that they are an accurate representation of real-world sounds, they are inherently more complex, variable, and aperiodic. Consequently, with natural tokens it is difficult to study how specific physical characteristics are represented at a subcortical level. Having precise control over the stimulus parameters is especially important when multiple stimuli are compared across a single dimension. For example, /b /, /d / and /g / can be distinguished based on their differing second formant trajectories (F2). However, natural utterances of /b /, /d / and /g / vary on more parameters than simply F2. In these cases, investigators rely on speech synthesizers such as Klatt to create stimuli with precisely defined time-varying and sustained features.

In the case of the F0, programs such as STRAIGHT and Praat can be used to remove aperiodicities, raise or lower the F0, or apply a particular time-varying pitch contour. To generate stimuli with pitch contours, hybrid stimuli can be made by manipulating the F0 of a natural speech token or combining two natural speech tokens using the PSOLA method in a program like Pratt.

Due to the increased prevalence of computer-made music, a large number of tools are currently available to generate music stimuli. A choice of a right tool depends on the desired trade-off between acoustic control and sound naturalness. Strict acoustic control of the stimuli can be best achieved through additive synthesis in programming environments like MATLAB (The Mathworks, Natick, Mass.). Acoustic samples of real instruments, which can be found in some music software packages (e.g., Garritan Personal Orchestra in Finale software, MakeMusic, Inc.), are another source for music stimuli. An intermediate solution is to use synthesizers, many of which are available as plugins for music software like Cubase Studio (Steinburg Media Technologies).

It can be difficult to construct synthetic sounds with strong affective quality. Thus, natural recordings such as those available from the Center for the Study of Emotions and Attention (University of Florida, Gainesville, Fla.) can be used to study paralinguistic aspects of sounds. Similarly, for environmental sounds, a stimulus can be selected from a corpus of natural sounds (e.g., Series 6000 General Sound Effect Library, a royalty-free CD of environmental sounds (Sound Ideas, Ontario, Canada)).

Stimulus Presentation

This section covers topics relating to stimulus presentation including stimulus intensity; monaural and binaural stimulation; left and right ear stimulation, stimulus polarity, stimulation rate; transducers (i.e., earphones, loudspeakers); jitter in the stimulus presentation, and multiple stimulus conditions.

Intensity

Speech, music and other complex sounds are typically delivered supra threshold within the "conversational" range of 60 to 85 dB SPL. Like the familiar click-ABR, cABRs are also intensity-dependent. This necessitates that the intensity be stable across subjects and recording sessions. Before each test session, the output intensity should be calibrated using a sound level meter with a coupler that enables the output to be measured directly from the insert earphones.

Using a /b / syllable, timing of a speech-evoked onset response and speech-evoked FFR (elicited by the same stimulus) can vary as function of intensity (e.g., 0 to 60 dB SL, in 10 dB increments). Consistent with the click-ABR and tone-evoked FFR literature, both response components showed systematic latency shifts with increasing intensity. However, the FFR peaks showed a steeper latency-intensity function than the onset response, suggesting that the onset response and speech-evoked FFR reflect distinct neural processes. Using a similar design, cABRs can be recorded to steady-state vowels between 55 dB nHL and 85 dB nHL (in 10 dB increments), in which harmonics in the formant range are clearly represented for each intensity. Although the amplitudes of the individual harmonics tended to increase with increasing intensity, the trajectory was not identical for all harmonics, nor was the increase always linear. Taken together, this work suggests that different components of the cABR are distinctively impacted by intensity level.

Monaural and Binaural Stimulation

When a sound is heard with both ears, it is perceived to be louder than when the same sound is presented at the same intensity to just one ear (theoretically binaural loudness summation is estimated to be 6 dB). Because the auditory brainstem plays an integral role in binaural processing, binaural interaction effects have been studied in the click-ABR and tone-FFR literature. Although similar parametric experiments have not been conducted for more complex stimuli, the same principles are assumed to apply. For practical reasons, binaural stimulation is preferable when testing adults, not only because it leads to larger and more robust responses, but also because it is more realistic in that we usually listen with both ears. However, monaural stimulation is used for individuals with asymmetric hearing thresholds, children and other populations who have difficulty sitting still during testing, or when the subject must to attend to another sound.

Left and Right Ear Stimulation

Left and right-ear stimulation produce similar, yet not identical ABRs responses. In fact, a right-ear advantage for speech is evident for discrete components of the speech-ABR, indicating that separate norms should be developed for the left and right ears.

Stimulus Polarity

Periodic sound waves traveling through air consist of alternating regions of compression (e.g., condensation) and decompression (e.g., rarefaction) of air molecules. In a time-amplitude plot of a sound wave, condensation and rarefaction manifest themselves as positive or negative deflections (respectively) from the baseline. Because clicks consist of a single positive or negative deflection, they are defined as either having condensation or rarefaction polarity. However, because periodic sounds oscillate between condensation and rarefaction states, the same terminology is not used. To convert a stimulus from one polarity to another, the waveform is shifted by 180 degrees (e.g., multiplied by −1).

When collecting cABRs, two different approaches can be followed: (1) record the response to a single stimulus polarity or (2) record responses to both polarities and either add or subtract responses to the two stimulus polarities. The process of adding will accentuate the lower-frequency components of the response including phaselocking to the amplitude envelope and minimize stimulus artifact and the cochlear microphonic (CM). Subtracting will bias the higher-frequency components by maximizing the spectral response, although this process can also maximize artifact contamination. It should be noted that both the addition and subtraction methods and single-polarity stimuli can be used.

Presentation Rate

Presentation rate depends on the length of the stimulus and the ISI (defined as the period of silence between the offset of one stimulus and the onset of the next). A second way to express the interval of presentation is stimulus onset asynchrony (SOA), which is measured from the onset of one stimulus to the onset of the next. The two measures are essentially the same for click stimulation, as a click has virtually no duration, but ISI and SOA are very different for cABRs. While there is no specific formula for determining the optimal ISI for a given stimulus length, the ISI has varied from ~30% of the stimulus length to more than double the length.

When choosing an ISI the following considerations should be made: First, changing the ISI can alter the perception of a complex sound. Second, if the ISI is not sufficiently long, the response to one stimulus may not fully conclude before the next stimulus is presented. Thus, the ISI and the duration of the averaging window should be long enough to allow for the response to return to baseline. The ISI should also allow for an ample sample of the baseline (e.g., non-stimulus-related) activity so that signal-to-noise ratios (SNRs) can be evaluated. Third, latencies and amplitudes, particularly of onset responses, are affected by rate of presentation. Although rate effects have not been extensively explored in FFRs to tones or complex stimuli, in adults speech-evoked FFR latencies seem to be less susceptible to rate changes than onset responses in adults. Fourth, to avoid contamination from the AC line frequency (e.g., 60 Hz in North America, 50 Hz elsewhere), a presentation rate should be chosen such that the rate divided by the line frequency is not an integer (e.g., for both 50 and 60 Hz line noise, 10/sec is a bad choice, but 10.3 or 11 is okay). Alternatively, a variable ISI should be used. Fifth, when conducting simultaneous cABR-cortical EP recordings longer ISIs may be required to obtain robust cortical auditory EPs.

An alternative approach is to record cABRs in several blocks of continuous stimulation (e.g., no silence between stimuli) using the same procedure used to record auditory steady-state responses. This technique maximizes spectral resolution at the expense of temporal resolution.

Transducer

Because circumaural headphones increase the chances for stimulus artifact contamination, electromagnetically shielded insert earphones (e.g., E•A•RTONE3A (Aearo Technologies, Minneapolis, Minn.), ER-3a (Etymotic Research, Inc., Elk Grove Village, Ill.), Bio-logic insert-earphones (Bio-logic Systems Corp., Mundelein, Ill.)) can be used with better effect. When testing persons with hearing aids or other populations not suited for inserts (e.g., cochlear implant wearers), loudspeakers can be used to deliver the stimulus. However, sound field delivery, causes the latency of the response to be more variable because the sound intensity changes subtly with head movements. To reduce or minimize head movements, a subject should focus on a movie or another visual image positioned directly in front of him/her. Also, because the latency is dependent on the distance between the loudspeakers and the subject, the location of the chair and speakers is carefully measured and marked, and the left and right speakers are positioned equidistantly.

Detecting Stimulus Jitter

One of the defining characteristics of the auditory brainstem response is that it reflects extremely fast neural activity synchronized across populations of neurons, with minute disruptions in neural precision being indicative of brainstem pathologies. For this reason, the delivery and recording units must be precisely time-locked to each other. Even a small amount of jitter in this synchronization can ruin an ABR recording. If the timing of the stimulus does not always occur at the same time with respect to the triggering of the recording system, the response is canceled, or at the very least becomes distorted, when trials are averaged. Thus, when a new recording system is acquired, it is important to confirm that the delivery system is properly calibrated to ensure that there is not an unexpected stimulus delay or jitter. A system that has been optimized for collecting cortical responses should also undergo testing before it can be cleared for brainstem testing. Because cortical responses rely less on absolute precision of stimulus timing, jitter may only be evident when recording brainstem responses.

To determine whether the stimulus presentation is jittered, couple the output of the delivery system into the electrode box, as if recording cABRs from a subject. Next, play a click stimulus and record the output into the recording system in continuous (e.g., non-averaging) mode. Adjust the output intensity, if the waveform is clipped in the recording. Recording a sizeable number of sweeps (e.g., 100+) can help ensure that the jitter does not creep in over time. After the recording is complete, check that each click occurs at the same time relative to the trigger across the recording. In an example, for a properly functioning system, the deviation should not exceed 0.1 ms. This is also an opportunity to determine whether the stimulus is actually simultaneous with the trigger or whether there is a delay that needs to be taken into account when processing and analyzing cABRs.

Multiple Stimulus Conditions

When an experiment includes multiple stimulus conditions, a block or interleaved paradigm can be used. In a block paradigm, each condition is presented separately (e.g., block 1: P P P; block 2: Q Q Q) and in an interleaved paradigm the stimulus conditions are intermixed (e.g., P Q P Q P Q or P Q P P Q P, etc.). In the blocked design, state (e.g., alertness) or expectancy effects may confound comparisons across stimulus conditions. However, if the delivery system is not designed to play multiple stimulus tokens, interleaving stimulus conditions may not be possible. While the presentation software might limit the number of stimuli that can be interleaved, there does not seem to be a corresponding neurophysiologic limit (e.g., in one experiment eight different stimulus conditions can be interleaved, two polarities for each, for a total of 16 different sounds). In the case where multiple stimuli are to be directly compared, it may be desirable to normalize the duration and amplitude across the stimulus set. This can be carried out in programs such as Level 16 and Praat.

Block and interleaved designs may invoke different online context-dependent subcortical encoding mechanisms. For example, the response can be compared to [d] collected in a block condition and the response to the same stimulus when it was presented with a pseudo-random probability within a mix seven other speech stimuli. The response to the interleaved condition was found to have smaller spectral amplitudes compared to the blocked condition, which the authors interpret to an indication of weaker stimulus 'tagging' when the stimulus is presented less frequently.

cABR Collection

Issues relating to electrodes, filtering, sampling rate, signal averaging, simultaneous ABR-cortical EP recording, artifact reduction, and recording conditions are reviewed below.

Electrodes and Electrode Montage

For cABRs, a vertical one-channel montage is the most common configuration. This configuration requires only three electrodes corresponding to the active (e.g., non-inverting), reference (e.g., inverting) and ground electrodes. Example electrode placements are Cz (active), ipsilateral earlobe (reference), and forehead or contralateral earlobe (ground). In the example, the earlobe rather than the mastoid is used because it is a non-cephalic site that causes fewer artifacts from bone vibration. For researchers who intend to record subcortical and cortical potentials simultaneously, or who wish to collect them within the same session, cABRs can be recorded with an electrode cap.

Filters

Filtering is used to isolate subcortical activity from cortical potentials and to increase the SNR of the response. For cABRs, the bandpass filters match the range of settings used for click-ABRs and typically fall in the range of 100-3000 Hz. This frequency range has been found to maximize the detection of the high-frequency transient peaks, such as the click-evoked peaks I-V, which have very sharp slopes. For stimuli containing frequencies below 100 Hz (or which produce distortion products below 100), the high pass cutoff should be lowered to ensure that none of these lower-frequency features are lost. Another approach is to record with more open filters such as 30-3000 Hz.

Sampling Rate

Sampling rate (Fs), also referred to as the digitization rate, determines how many times per second the analog neural signal is digitally sampled by the recording system. In cases where only low-frequency components of the response are of interest, a low Fs (e.g., 1000-2000 Hz) may be appropriate. However, many researchers opt to over-sample cABR recordings (e.g., rates range from 7 kHz to 50 kHz) by sampling well above the Nyquist frequency (e.g., twice the highest frequency in the stimulus). In addition to reducing sample errors, a higher Fs, by definition, increases the temporal precision of the recording and allow for finer differentiation of response peaks. Because cABR disruptions and enhancements occur on the order of tenths of milliseconds, fine-grained temporal precision is essential. Although a higher Fs is desirable, the choice may be limited by the particular recording system. For example, some recording systems utilize a fixed number of sample points. In this case, the Fs is dependent on the duration of the recording window (Fs=sample points/duration).

Signal Averaging

An age-old question in the EP literature is how many sweeps must be averaged to obtain a robust and reliable response. It is well established that for higher intensity stimuli roughly 1000-2000 sweeps are needed to collect click-ABRs and FFRs to tones. For cABRs a comparable but sometimes greater number of sweeps are obtained (e.g., 1000-6000). However, if analyses are only carried out in the frequency domain, then spectral maxima may be detected (e.g., statistically above the noise floor) with fewer sweeps.

Certain examples collect more stimulus trials than less, e.g., ~2000-3000 per polarity (e.g., 4000 to 6000 total sweeps). There are several reasons for this strategy. First, this allows for the creation of sub-averages that can be used to determine response repeatability and/or track how the response evolves over time. Second, subtle response characteristics and small group differences that may not be apparent until additional sweeps are collected and/or repeatability is confirmed may be interesting. A general principle of EP signal averaging is that the SNR is proportional to the square root of the number of sweeps. Thus, the overall SNR increases quickly at first and then begin to plateau with more sweeps. However, an individual component of the cABR (for example, a specific peak in the time domain or a spectral peak that is near the phaselocking limits of the brainstem) may show its own SNR progression with different response components requiring greater or fewer sweeps. While it may not be possible to determine the "optimal" number of sweeps for a given stimulus and population before the start of an experiment, an interesting or optimal range can be deduced a posteriori using an iterative off-line averaging technique based on a handful of subjects from whom a large number of sweeps have been collected (e.g., compare subaverages of 1000 sweeps, 1500 sweeps, 2000 sweeps, . . . 6000 sweeps, etc.). Better characterization of the cABR can enable the number of sweeps to be reduced while still maintaining spectral and temporal precision.

In the time-domain, the averaging window should be long enough to include a pre-stimulus baseline period, the response period, and a post-stimulus period. The length of the post-stimulus time window needs to account for the stimulus transmission delay and neural conduction time. A post-stimulus period between 10 ms and 50 ms is recommended to ensure that the response returns to baseline. The pre-stimulus baseline reflects the ambient EEG before the response, thereby assisting in the interpretation of the response. For example, when identifying prominent peaks in the response waveform, peak amplitudes are compared to the amplitude of the pre-stimulus period. For a given peak, if the amplitude does not exceed the baseline amplitude, it is not considered a valid (e.g., reliable) peak. The baseline period can also be used to determine the SNR (in the time and frequency domains). For running window analyses, it is helpful to have a pre-stimulus period that is long enough to include one full analysis window. Because running window analyses are performed on 40 ms bins in the example, a pre-stimulus window of at least 40 ms is used.

Simultaneous cABR—Cortical Recordings

There are a number of practical limitations to simultaneously recording cABR and cortical responses that arise from cABRs and cortical EPs having different optimal recording parameters. First, cABRs require a much higher Fs than cortical responses (often a tenfold or more difference). Second, because cortical responses are optimally obtained using slower stimulation rates than ABR, the presentation rate must be slow for simultaneous recordings. Yet because cABRs are much smaller in amplitude (e.g., less than 1 microvolt), more trials must be collected for a robust cABR than for a cortical response, often leading to long recording sessions. These factors aggregate to create extremely large files, especially when high-density electrode caps are used, leading to concerns about both computer processing power and data storage. For these reasons, brainstem and cortical-evoked responses can be collected in separate recording sessions, optimizing recording lengths, numbers of channels, and sampling rates for each.

Avoiding, Detecting and Eliminating Artifact

There are four types of artifact that can distort the auditory brainstem response recordings: external (e.g., non-biological) electrical noise, myogenic (muscular) artifact, cochlear microphonic (CM), and stimulus artifact. While artifacts can be minimized, it is best to remove the contamination at its source.

When combating electrical artifact such as line noise (60 or 50 Hz), the best tactic is to record within an electrically shielded booth and remove all electrical sources from the booth including televisions, CRT and LCD computer monitors. Light dimmers are another serious source of noise. If the experimenter wishes to play a movie or another visual stimulus during the experiment, two different approaches can be taken. The cheaper option is to use a portable battery-powered DVD player that is placed on a table in front of the subject. The second option, and the one we employ most often, is to use an LCD projector located outside the booth that projects the visual stimulus through a booth window onto a screen inside the booth.

Another type of electrical artifact comes from the electrical trigger pulse that is used to synchronize stimulus presentation and response averaging. This artifact appears at time zero. If a long trigger is used a second artifact may appear when the trigger turns off. If the duration of the trigger pulse can be manually set within the stimulus presentation software, this type of artifact can be reduced by either shortening the trigger pulse so it occurs before the onset of the response (e.g., <5 ms), or by elongating it to be longer than the stimulus itself.

Given that cABRs are typically recorded with wide bandpass filters, myogenic artifacts are often not filtered out. Because myogenic artifacts produce potentials that can be many times larger than the brainstem response, trials for which the amplitude exceeds a specific threshold should be excluded from the final average (either on-line or off-line). For example, this threshold ranges from +/−20 to +/−75 μV. Although this technique removes large artifacts, it does not completely expunge all myogenic contamination from the recording. For this reason, it is important to keep the subject relaxed and still during the recording session.

The CM is a potential generated by the cochlear hair cells which, like the FFR, mimics the temporal waveform of the acoustic stimulus. Because of its similarity to the neural response, care must be taken to prevent or remove the CM from the recordings. The CM can be distinguished from the brainstem response in a number of ways. Unlike the cABR, which occurs at approximately 6-10 ms post-stimulus onset, the onset of the CM is nearly coincident with the stimulus. The cochlear microphonic and cABR are also differentially affected by rate, intensity and noise. For example, while cABRs break down with increases in presentation rate and simultaneous masking intensity, the CM remains unaffected. Furthermore, in contrast to cABR amplitude, which plateaus at supra threshold levels, the size of the CM usually increases linearly with moderate increases in intensity.

Given that the cABR occurs within a matter of milliseconds after stimulation, and the fact that the cABR closely mimics the stimulating waveform, stimulus artifact is a major concern. Fortunately, this type of artifact is easy to detect and with the right recording techniques can be minimized.

In most modern EP collection systems, the stimulus waveform is sent as an electrical signal to a transducer where it is converted to an acoustic signal. If the transducer is not properly shielded, the electrical signal can "leak" and get picked up by the electrodes and recorded by the EP system along with the response. In addition to using electromagnetically shielded earphones, it is also good practice to double-check that the electrode leads and transducer cables are not touching and to also position the electrodes and transducer as far apart as possible. This can be achieved with insert earphones that use a plastic tube to separate the transducer and foam earplug. Using longer tubes and/or positioning the transducer outside the test booth can further minimize stimulus artifact.

Given that both artifacts follow the phase of the stimulus exactly, stimulus artifact and CM can be reduced or minimized from the response by adding responses to alternating stimulus polarities.

Active vs. Passive Test Conditions

Because ABRs are not greatly affected by sleep, click-ABRs are often collected while the patient is asleep or sedated. Similarly, to reduce muscular artifact, many cABR researchers allow or even encourage their subjects to fall asleep on a cot or to recline comfortably in a chair. In order to rule out differences in state as a potential confound, our subjects stay awake during testing. To promote relaxation and stillness, subjects watch a movie or read a book. For monaural stimulation, the movie soundtrack is played at a low level (e.g., ~40 dB SPL) so that it can be heard in the non-test ear without masking the auditory stimulation. Subtitles are displayed for binaural recordings.

cABRs can also be recorded under active test conditions in which the subject performs a task (e.g., detecting/counting oddball stimulus tokens). For example, using an audiovisual paradigm, active multi-sensory integration can shape how subcortical sensory processes respond to speech and music. While there is some disagreement as to whether attention modulates the click-ABR, attentional state can govern the FFR to tones and speech. This is consistent with recent functional MRI work showing that selective auditory attention tasks can modulate the activation of subcortical structures.

Notably, to study the dynamic nature of auditory processing, the subject need not be performing an active task during data collection. A growing body of research supports the use of passive recording conditions to study how brainstem function is fine-tuned by experience. Although the subject is not actively processing the sounds evoking the response, cABRs tap into how previous active engagement with sound has shaped brainstem processes over the course of lifelong or short-term auditory experiences. This refinement of the sensory system likely results from an interplay between subcortical structures and high-order cognitive processes via the corticofugal system.

Data Analysis

To analyze the transient and sustained aspects of cABRs, a battery of measures are employed to appraise the timing and magnitude of neural synchrony, as well as the strength and precision of phaselocking. Because cABRs are rich in temporal and spectral information, the use of multiple measures allows users to (1) dissect individual components of the response and how they reflect distinct aspects of processing and (2) describe brainstem encoding in a holistic manner. Due to transparency between the temporal and spectral features of the stimulus and the response, our analyses are largely stimulus-driven. That is to say, analyses and interpretation can be based on the acoustic make-up of the stimulus. Because of this stimulus-response fidelity, commonly employed digital signal processing tools such as cross-correlation and Fourier analysis can be used to analyze both the stimulus and response. Each of these techniques comes in many variants and each belongs to a large family of analysis methods.

This section includes an overview and illustration of the most common signal processing techniques used to evaluate cABRs, namely peak latency and amplitude measurements, root-mean-square (RMS) amplitude, cross-correlation and Fourier analysis. In certain examples, the analyses described below are performed offline on the averaged time-domain response or sub-averages. Although some of these measurements can be made directly by the EP collection unit, others require the use of computational software packages such as MATLAB (The Mathworks, Natick, Mass.).

Analyzing Transient Responses

To characterize the transient features of the response, individual response peaks relating to major acoustic landmarks in the stimulus are identified. For each peak, latency (e.g., time relative to stimulus onset) and amplitude measurements are obtained. Inter-peak measurements are also calculated; these include inter-peak amplitude, duration, slope and area. In general, transient peaks occur within 6-10 ms after the corresponding stimulus landmark. Automated peak-picking algorithms can be used to objectively identify maxima (peaks) or minima (troughs) known to occur within a given latency range. To be considered a reliable peak, the absolute amplitude is to be larger than the baseline activity recorded prior to the onset of the stimulus. Confidence in selection of ambiguous peaks is aided by referring to sub-averages. Once the peaks have been identified, they are visually confirmed or rejected by multiple raters who are blind to subject group and/or stimulus contrast(s). When the raters disagree, the selection is determined by the most experienced rater. However, agreement among raters may reflect common training in peak identification. Consequently, if peaks cannot be identified by objective methods, an external rater should also be consulted whenever feasible.

A number of techniques have been developed to aid in the identification of difficult to identify/low-amplitude peaks. These include wavelet denoising and high-pass filtering. When determining which peaks to pick in the cABR a novel stimulus, start by generating a grand average response of all subjects, and then compare the grand average to the stimulus waveform to determine where the two waveforms match up. Once this has been performed, the individual waveforms should be reviewed to determine which peaks have high replicability across subjects (e.g., <1 ms deviation across subjects/groups).

When multiple stimulus conditions are compared, a more advanced technique involves calculating the latency changes between/among conditions as a function of time. For example, formant frequency differences differentiating the stop consonants /b/, /d/ and /g/ are represented by systematic and progressive latency differences in the cABR with /g/ responses occurring first, followed by /d/ then /b/ (e.g., higher stimulus frequencies yield earlier response latencies). These latency differences can be visualized using a latency-tracking plot.

Analyzing Sustained Responses

The response to periodic features (e.g., steady-state vowels, formant transitions, pitch contours, steady-state musical notes, glissandos) can be analyzed using RMS, cross-correlation and Fourier analysis. Each of the analysis techniques described below can be used to perform "static" window or "sliding" window (also called running window) analyses. A single region of the time-amplitude waveform is evaluated in a static window analysis. For sliding-window analyses, small time bins (e.g., windows) of the signal are analyzed in succession. The technique captures how the signal changes over time and it is often used to create a three dimensional representation of the signal, such as spectrograms and correlograms. For time-frequency-varying stimuli such as Mandarin pitch contours, diphthongs and glissandos, "frequency tracks" are generated using sliding window analysis to capture how the changing F0 or harmonic is tracked in the response over time.

For cABRs, RMS amplitude represents the magnitude of neural activation over a given time period. RMS is calculated by (1) squaring each point, (2) finding the mean of the squared values and then (3) taking the square root of the mean. The quotient of response RMS amplitude (e.g., signal) and pre-stimulus baseline RMS amplitude (e.g., noise) can serve as a measure of signal to noise ratio. If the SNR is less than 1, the pre-stimulus activity is larger than the "response" activity. In cases where the SNR of the cABR is less than 1.5, the cABR can be recollected, or the subject can be excluded. A typical cABR has an SNR is in the range of 2.5 to 3, although SNRs as high as 6 are not uncommon.

Correlation is a useful tool for comparing the overall morphology and timing of two signals (e.g., stimulus vs. response). In general terms, cross-correlation determines the extent to which two signals are correlated, as a function of the time shift between them. At a given time displacement, if two signals are identical, the cross-correlation coefficient (r) is 1. If the signals are identical but 180° out of phase, it is −1. However, if the signals are completely dissimilar, r=0. In addition to using cross-correlation to determine the degree of similarity, it can also be used to quantify the time delay between two signals (e.g., time displacement that produces the greatest r-value). The onset of the response can be objectively determined in this manner by correlating the stimulus and the response. In addition, two responses can be cross-correlated to determine how much the response has been degraded in noise or how the response changes for different stimulus conditions, e.g., left vs. right ear stimulation. When performing stimulus-to-response correlations, the stimulus is low pass filtered to remove the high frequencies that are not present in the response and then resampled to match the sample rate of the response.

Cross-correlation can also be used to find repeating patterns (e.g., periodicities) within a signal, such as the fundamental periodicity and the temporal envelope. This class of cross-correlations is called autocorrelation because a signal is correlated with itself. Autocorrelations are performed by making a copy of a signal and then shifting the copy forward in time.

The fundamental frequency is represented in the stimulus and cABR by peaks occurring at the period of the F0 (period=1/frequency). The interpeak interval (period) can be found by calculating the time shift at which the signal best correlates with itself. Thus, autocorrelation is an objective way for determining interpeak intervals and can be used to estimate the F0 of the response (calculated as 1/d, where d is the time shift needed to obtain the maximum autocorrelation). The strength of phaselocking to the F0 can also be estimated by this maximal correlation coefficient value. In addition, autocorrelation functions that have broader morphology reflect less robust responses, and steeper functions reflect sharper and more robust phaselocking.

An autocorrelogram, created via sliding window analysis, is a visual representation of how well the signal correlates with itself across time. In a three dimensional graph, the degree of correlation is represented in color, with the vertical axis representing the time shift and the horizontal axis representing time. Autocorrelograms can be used to evaluate frequency-tracking to the F0 and amplitude envelope. Phase-locking can then be described in terms of consistency (e.g., how much the maximum r-value deviates over time) and strength over time (e.g., the average maximum r-value over time).

A frequency domain representation of the cABR can be generated using Fourier analysis. This method can be used to measure the precision and magnitude of neural phaselocking at specific frequencies or frequency ranges.

One property of periodic waveforms is that when two or more waves interact, the resulting waveform is the sum of the individual components (assuming a linear system). This is the principle underlying Fourier analysis. Using Fourier analysis, a complex waveform consisting of many frequency components is decomposed into a set of sine waves. The magnitude of each sine wave corresponds to the amount of energy contained in the complex waveform at that frequency. The spectral composition of a complex wave can then be represented by plotting the frequency of the sine wave on the x-axis and the magnitude on the y-axis. The fast Fourier transform (FFT) is the most common algorithm for performing spectral analysis although other Fourier-based methods have been used by cABR researchers. The FFT is most efficient (e.g., faster) when the signal N (defined as the number of points) is a power of two. However, software such as MATLAB (The Mathworks, Natick, Mass.) and Mathematica (Wolfram Research, Inc., Champaign, Ill.) do not require the input to be a set length. Fourier analyses can also be used to generate a frequency-domain average. An alternative, less computationally demanding technique, is to perform an FFT on the time-amplitude average.

When dealing with finite signals such as cABRs, the frequency resolution is dependent on the duration of the sample being analyzed (resolution=1/T, where T=duration in sec). For a 50 ms signal, the frequency resolution is 1 sample per 0.05 sec or 20 Hz. The resulting frequency spectrum contains information only at integer multiples of 20 Hz (e.g., 0, 20, 40, 60 . . . Nyquist frequency; 0 Hz=DC component). If the signal contains a frequency component at 130 Hz, the amplitude of the 130 Hz component, which is not an integer multiple of the sampling period, "leaks" into the neighboring components (e.g., 120, 140, etc.). This leakage can be reduced by increasing T. As a general rule of thumb, T should be long enough to include a minimum of 2 to 4 cycles of the lowest frequency of interest. For example, if you wish to characterize a 100 Hz frequency component, the length of the signal should be at least 20 ms (i.e., (1/100)×2). One trick for "increasing" T, without actually taking a longer sample of the signal, is to add a series of zeros to the end of the original sample (often called zero padding). For example, if the 50 ms sample has a 20 kHz sample rate (e.g., 1000 point sample), to increase the resolution from 20 Hz to 1 Hz, 19,000 zeros are added onto the end of the sample before performing the FFT.

Another thing to consider when performing Fourier analyses is that the FFT treats the sample as if it were a continuous loop, in which the first and last samples are contiguous. Thus, if the starting and ending amplitudes are not the same, the amplitude difference gets reflected in the FFT output. When the discontinuity is large, it creates a click-like feature in the response. Because clicks are broadband, this discontinuity results in frequency splattering that contaminates the accuracy of the spectral analysis. In order to prevent this splatter, a common countermeasure is to multiply the signal by a windowing function, which tapers the amplitudes on both ends, so that the sample begins and ends at zero with zero amplitude. Window functions come in many different shapes, such as a Hanning window, which has a bell-shaped function.

For cABRs, frequency spectra are analyzed with respect to the frequency composition of the stimulus. Because stimulus and response amplitudes occur on different scales, the amplitudes must be normalized in order to plot the two spectra on the same plot. This can be achieved by converting both spectra to decibels or by dividing each spectral amplitude by the corresponding spectral maximum. When analyzing the response in the frequency domain, spectral maxima corresponding to the stimulus F0 and its harmonics are identified, and the phase and amplitude (modulus of the FFT) of the maxima are recorded. Fourier analysis is also useful for calculating the amplitude over a range of frequencies, especially in cases when the stimulus has time-varying features such as formant transitions. By performing an FFT on the pre-stimulus time window, the spectral noise floor can be estimated and used to calculate spectral SNRs.

If performed as part of a sliding-window analysis, the FFT can be used to generate a spectrogram, a three dimensional graph of the frequency spectrum as a function of time. This type of analysis is often referred to as Short-Term Fourier Transform (STFT). In these plots, the horizontal axis (x-axis) represents time, the vertical axis (y-axis) represents frequency and the third dimension represents the amplitude at a given time-frequency point. The third dimension is usually represented using a color continuum. Frequency-tracks can be derived from STFTs of the response. Wavelets provide an alternative method for performing time-frequency analyses.

Thus, auditory brainstem responses provide an objective and non-invasive means for examining how behaviorally relevant sounds such as speech and music are transcribed into neural code. The brainstem response is ideal for studying this process because stimulus features are preserved in the response. Notably, this process is not "hard coded". Brainstem encoding of speech and other complex signals is shaped by short-term and lifelong musical and language experience and is thereby tightly coupled with higher-order cognitive processes. Aspects of the response are selectively impaired or enhanced in impaired and expert populations (e.g., children with reading impairments and musicians) facilitating the delineation of specific underlying processes. Like click-evoked auditory brainstem responses, cABRs are well suited for clinical applications because they can be meaningfully applied to individuals. A variety of speech and musical stimuli have been used to evoke auditory brainstem responses. When choosing a stimulus, the acoustic properties of the stimulus matter. To maximize transient responses, the sound should have sharp onsets/amplitude bursts. A low pitch stimulus (e.g., <300 Hz), or a stimulus with its fundamental periodicity in this range, is used to obtain strong phaselocked (i.e., sustained) responses to the F0 and harmonics. cABRs are generally elicited at supra threshold levels (e.g., 60-80 dB SPL) using monaural or binaural stimulation via electromagnetically shielded insert earphones. If the stimulus presentation is jittered by even a small amount, cABRs are canceled when trials are averaged. cABRs can be recorded using the same data acquisition procedures as click-ABRs and tone-FFRs. Additionally, manipulations of stimulus polarity can be used to enhance different aspects of the response and to minimize stimulus artifacts and the CM. Because of the transparency between the stimulus and response, digital signal processing tools (e.g., cross-correlation, Fourier analysis) can be used to analyze both the stimulus and response. Sliding-window analysis is used to track how the response changes over time.

Neural transcription of sound in the auditory brainstem and midbrain is arguably a measure of auditory processing and as such can be applied to research and clinical assessment whenever auditory processing is of interest. This includes the investigation of auditory specialization (e.g. musicians, native language speakers) and the management of auditory disorders (e.g. auditory processing disorders, language-based learning impairments such as dyslexia, specific language impairment and autism, hearing loss and age-related hearing decline) that result in pervasive difficulties with speech perception in noise. Auditory brainstem responses to complex sounds provide an objective neural metric for determining the effectiveness of remediation strategies, providing the outcome measures that clinicians can use to strengthen their role in advocating for auditory training and remediation across the lifespan. The cABR has reinforced the notion that a contemporary view of the auditory system includes its cognitive and sensory functions. That is, subcortical function reflects a confluence of sensory and cognitive processes that likely operate in a reciprocally interactive manner. This view can help the field of audiology more effectively address socially and clinically meaningful aspects of human communication.

Example Methods of cABR Collection

Figure 15:
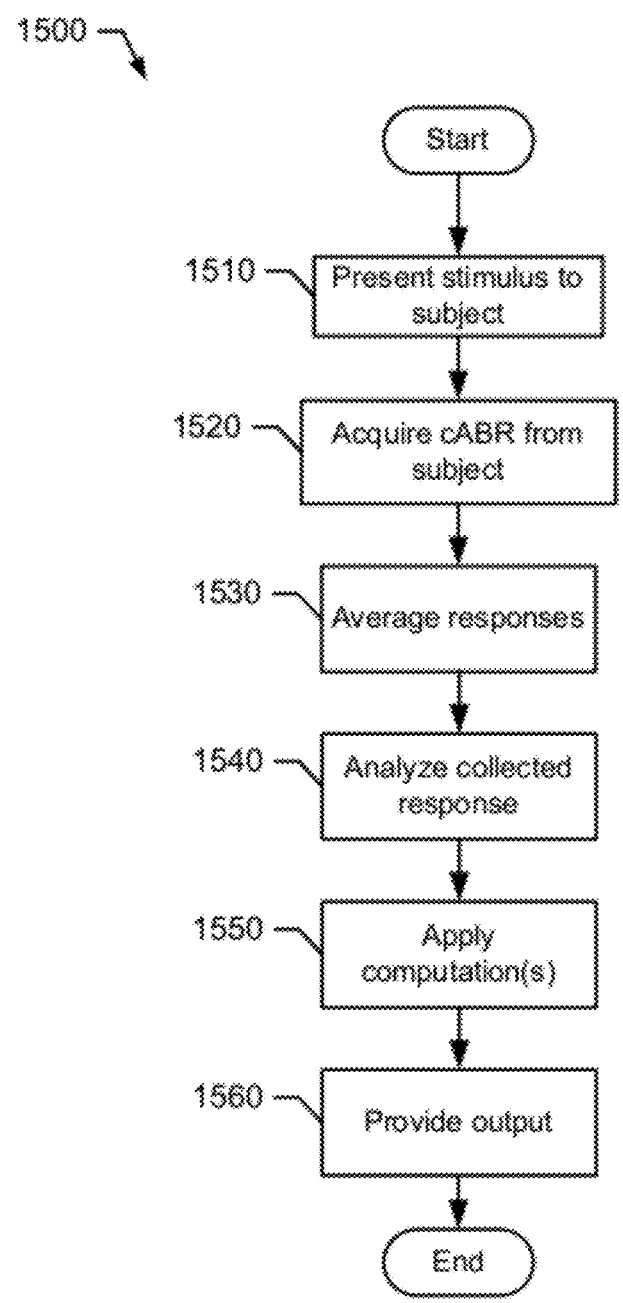
FIG. 15 depicts a flow diagram of an example method to evaluate auditory brainstorm response to complex sounds using a set of collection and analysis tools.

FIG. 15 depicts a flow diagram of an example method 1500 to evaluate auditory brainstorm response to complex sounds (cABR) using a set of collection and analysis tools (a cABR Toolbox) such as those described herein. At block 1510, one or more complex auditory stimulus is presented to a subject. For example, headphone(s) and/or other speaker(s) can introduce a stimulus to one or both ears of a subject.

At block 1520, the subject's cABR is acquired. For example, the subject's cABR can be acquired by collecting evoked potentials originating from the subject's brainstem (e.g., through use of electrodes).

At block 1530, responses are averaged to form a collected response. For example, responses can be averaged in the time and/or frequency domain. At block 1540, the collected response is analyzed in comparison to the stimulus/stimuli and/or other responses to provide a processed output. For example, the collected response can be provided to one or more digital signal processing routines to analyze all or part of the collected response (e.g., based on one or more of latency, amplitude, frequency, phase, etc.) and provide a processed output. The DSP routines can enable comparison(s) of the collected response to the one or more stimulus and/or other response(s), for example.

At block 1550, one or more statistical computations are applied to the processed output. For example, mean amplitude measurements, cross-correlation, frequency error, cross-phase analysis, etc., can be applied to the processed output. At block 1560, the processed output and/or associated computation(s) are provided to a user. For example, the processed output and/or computation(s) can be displayed, stored, provided to another application or analysis tool or other system, etc.

Example Processing System

Figure 16:
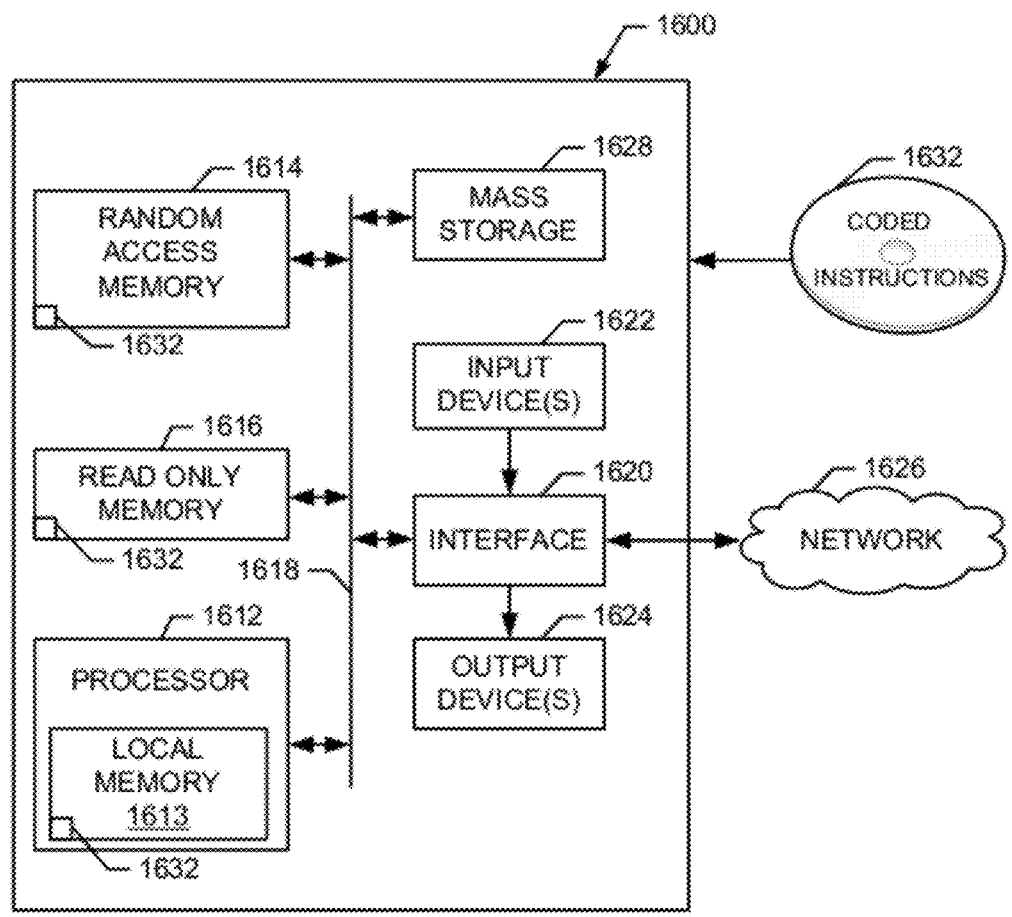
FIG. 16 is a block diagram of an example processor platform 1600 capable of executing instructions to implement the example systems, methods, views, and analysis recited herein.

FIG. 16 is a block diagram of an example processor platform 1600 capable of executing instructions to implement the example systems, methods, views, and analysis recited herein. The processor platform 1600 can be, for example, a server, a personal computer, an Internet appliance, a set top box, or any other type of computing device.

The processor platform 1600 of the instant example includes a processor 1612. For example, the processor 1612 can be implemented by one or more microprocessors or controllers from any desired family or manufacturer. The processor 1612 includes a local memory 1613 (e.g., a cache) and is in communication with a main memory including a volatile memory 1614 and a non-volatile memory 1616 via a bus 1618. The volatile memory 1614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1616 may be implemented by flash memory and/or any other desired type of memory device. Access to the main memory 1614, 1616 is controlled by a memory controller.

The processor platform 1600 also includes an interface circuit 1620. The interface circuit 1620 may be implemented by any type of interface standard, such as an Ethernet interface, a universal serial bus (USB), and/or a PCI express interface.

One or more input devices 1622 are connected to the interface circuit 1620. The input device(s) 1622 permit a user to enter data and commands into the processor 1612. The input device(s) can be implemented by, for example, a keyboard, a mouse, a touchscreen, a track-pad, a trackball, isopoint and/or a voice recognition system.

One or more output devices 1624 are also connected to the interface circuit 1620. The output devices 1624 can be implemented, for example, by display devices (e.g., a liquid crystal display, a cathode ray tube display (CRT), etc.). The interface circuit 1620, thus, typically includes a graphics driver card.

The interface circuit 1620 also includes a communication device such as a modem or network interface card to facilitate exchange of data with external computers via a network 1626 (e.g., an Ethernet connection, a digital subscriber line (DSL), a telephone line, coaxial cable, a cellular telephone system, etc.).

The processor platform 1600 also includes one or more mass storage devices 1628 for storing software and data. Examples of such mass storage devices 1628 include floppy disk drives, hard drive disks, compact disk drives and digital versatile disk (DVD) drives. The mass storage device 1628 may implement a local storage device.

Coded instructions may be stored in the mass storage device 1628, in the volatile memory 1614, in the non-volatile memory 1616, and/or on a removable storage medium such as a CD or DVD.

While certain examples have been illustrated in the attached figures, one or more of the elements, processes and/or devices illustrated can be combined, divided, re-arranged, omitted, eliminated and/or implemented in other ways. The flowchart of FIG. 15 can be interpreted to include blocks representative of example machine readable instructions for implementing some or all of the systems and methods recited herein. In certain examples, machine readable instructions can include a program for execution by a processor to implement systems and methods described herein. The program can be embodied in software stored on a computer readable medium such as a CD-ROM, a floppy disk, a hard drive, a digital versatile disk (DVD), a Blu-ray disk, or a memory associated with a processor, including any other storage media in which information is stored for any duration (e.g., for extended time periods, permanently, brief instances, for temporarily buffering, and/or for caching of the information), but the entire program and/or parts thereof could alternatively be executed by a device other than the processor and/or embodied in firmware or dedicated hardware. Further, although an example program is described, many other methods of implementing the example systems and methods (and/or one or more portions of the systems and methods) can alternatively be used. For example, the order of execution of the blocks can be changed, and/or some of the blocks described can be changed, eliminated, or combined. Additionally or alternatively, some or all of a method can be performed manually.

As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory or tangible computer readable medium is expressly defined to include any type of computer readable medium and to exclude propagating signals.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of collecting and analyzing complex auditory brainstem response, the method comprising:
   presenting at least one complex auditory stimulus to a subject;
   acquiring the subject's complex auditory brainstem response;
   averaging complex auditory brainstem responses from the subject in at least one of a time domain and a frequency domain to form a collected response;
   analyzing the collected response using a signal processor to process the collected response to provide a processed output and to adapt the response for comparison to the at least one complex auditory stimulus, the analyzing of the collected response including performing cross-correlations between complex auditory brainstem response waveforms to generate a cross-phaseogram including cross-phase analysis between responses; and
   performing statistical computations on the processed output to generate visual and data feedback for a user.

2. The method of claim 1, wherein presenting further comprises presenting at least one complex auditory stimulus to at least one ear of the subject.

3. The method of claim 1, wherein acquiring further comprises acquiring the subject's complex auditory brainstem response with an evoked potential collection system.

4. The method of claim 1, wherein analyzing further comprises analyzing the collected response using a digital signal processor to analyze the response based on at least one of latency, amplitude, frequency and phase and to enable comparisons of the collected response to the at least one complex auditory stimulus and other complex auditory brainstem responses.

5. The method of claim 1, wherein analyzing further comprises processing the collected response according to a time-amplitude domain with a time-amplitude waveform, the processing by the signal processor including at least one of a running moving average, root mean square and mean average analysis.

6. The method of claim 1, wherein analyzing further comprises processing the collected response according to a frequency-amplitude domain with a frequency spectrum over a user-defined time range, the processing by the signal processor including obtaining a spectral amplitude at a plurality of frequencies and generating a frequency-domain average.

7. The method of claim 1, wherein analyzing further comprises processing the collected response according to a time-frequency domain, the processing by the signal processor including analyzing a frequency spectrogram over a user-defined time range and extracting a frequency contour to calculate frequency tracking measurements.

8. The method of claim 1, wherein analyzing further comprises processing the collected response according to a lag-frequency domain to view and analyze an autocorrelogram over a user-defined time range and extract a pitch contour to calculate pitch tracking measurements.

9. The method of claim 1, wherein the at least one complex auditory stimulus comprises a plurality of syllables spoken in different intonations.

10. A tangible computer readable storage medium including computer program code to be executed by a processor, the computer program code, when executed, to implement a method of collecting and analyzing complex auditory brainstem response, the method comprising:
    presenting at least one complex auditory stimulus to a subject;
    acquiring the subject's complex auditory brainstem response;
    averaging complex auditory brainstem responses from the subject in at least one of a time domain and a frequency domain to form a collected response;
    analyzing the collected response using a signal processor to process the collected response to provide a processed output and to adapt the response for comparison to the at least one complex auditory stimulus, the analyzing of the collected response including performing cross-correlations between complex auditory brainstem response waveforms to generate a cross-phaseogram including cross-phase analysis between responses; and
    performing statistical computations on the processed output to generate visual and data feedback for a user.

11. The computer readable storage medium of claim 10, wherein presenting further comprises presenting at least one complex auditory stimulus to at least one ear of the subject.

12. The computer readable storage medium of claim 10, wherein acquiring further comprises acquiring the subject's complex auditory brainstem response with an evoked potential collection system.

13. The computer readable storage medium of claim 10, wherein analyzing further comprises analyzing the collected response using a digital signal processor to analyze the response based on at least one of latency, amplitude, frequency and phase and to enable comparisons of the collected response to the at least one complex auditory stimulus and other complex auditory brainstem responses.

14. The computer readable storage medium of claim 10, wherein analyzing further comprises processing the collected response according to a time-amplitude domain with a time-amplitude waveform, the processing by the signal processor including at least one of a running moving average, root mean square and mean average analysis.

15. The computer readable storage medium of claim 10, wherein analyzing further comprises processing the collected response according to a frequency-amplitude domain with a frequency spectrum over a user-defined time range, the processing by the signal processor including obtaining a spectral amplitude at a plurality of frequencies and generating a frequency-domain average.

16. The computer readable storage medium of claim 10, wherein analyzing further comprises processing the collected response according to a time-frequency domain, the processing by the signal processor including analyzing a frequency spectrogram over a user-defined time range and extracting a frequency contour to calculate frequency tracking measurements.

17. The computer readable storage medium of claim 10, wherein analyzing further comprises processing the collected response according to a lag-frequency domain to view and analyze an autocorrelogram over a user-defined time range and extract a pitch contour to calculate pitch tracking measurements.

18. The computer readable storage medium of claim 10, wherein the at least one complex auditory stimulus comprises a plurality of syllables spoken in different intonations and a plurality of musical notes.

19. A system comprising:

a transducer positioned with respect to a subject to provide a complex auditory stimulus to the subject in response to a trigger, the complex auditory stimulus to include a plurality of syllables spoken with different intonations and a plurality of musical notes;

a plurality of electrodes to detect a complex auditory brainstem response from the subject as a plurality of evoked potentials originating from the brainstem of the subject; and a processor to provide the complex auditory stimulus and trigger to the transducer and to process the complex auditory brainstem response from the plurality of electrodes, the processor to process the complex auditory brainstem response over at least one user-defined range to provide time and frequency domain analysis with cross-correlation and cross-phase analysis between a plurality of responses to provide a visualization and output to a user.

* * * * *